US008598195B2

(12) United States Patent
Almqvist et al.

(10) Patent No.: US 8,598,195 B2
(45) Date of Patent: Dec. 3, 2013

(54) PEPTIDOMIMETIC COMPOUNDS

(75) Inventors: Fredrik Almqvist, Umea (SE); Magnus Sellstedt, Umeå (SE); Pralay Das, West Bengal (IN)

(73) Assignee: Fredrik Almqvist (SE)

( * ) Notice: Subject to any disclaimer, the term of this patent is extended or adjusted under 35 U.S.C. 154(b) by 327 days.

(21) Appl. No.: 12/990,415

(22) PCT Filed: Apr. 30, 2009

(86) PCT No.: PCT/SE2009/050464
§ 371 (c)(1),
(2), (4) Date: Feb. 17, 2011

(87) PCT Pub. No.: WO2009/134203
PCT Pub. Date: Nov. 5, 2009

(65) Prior Publication Data
US 2011/0160241 A1    Jun. 30, 2011

Related U.S. Application Data

(60) Provisional application No. 61/048,976, filed on Apr. 30, 2008.

(51) Int. Cl.
C07D 417/14    (2006.01)
A61K 31/4365   (2006.01)
A61K 31/437    (2006.01)

(52) U.S. Cl.
USPC .......................................... 514/293; 546/83

(58) Field of Classification Search
USPC ................... 546/83, 82, 81; 514/294, 293
See application file for complete search history.

(56) References Cited

U.S. PATENT DOCUMENTS

2004/0214838 A1  10/2004 Carpino et al.
2007/0082887 A1   4/2007 Hultgren et al.

FOREIGN PATENT DOCUMENTS

FR            1463883 A      11/1966
WO         WO-96/12720 A1     5/1996
WO         WO-01/36426 A1     5/2001

OTHER PUBLICATIONS

Dorwald F. A. Side Reactions in Organic Synthesis, 2005, Wiley: VCH, Weinheim p. IX of Preface.*
Synthsis of a Novel Tricyclic Peptidomimetic Scaffold, Jul. 2008.*
Chorell, E., et al., "Diverse Functionalization of Thiazolo Ring-Fused 2-Pyridones", *J. Org. Chem*, 72, (2007), 4917-4924.
Dow, R.L., "Discovery of 2-(2-Chlorophenyl)-3-(4-chlorophenyl)-7-(2,2-difluoropropyl)-6,7-dihydro-2*H*pyrazolo[3,4-/] [1,4]oxazepin-8-(5*H*)-one (PF-514273), a Novel, Bicyclic Lactam-Based Cannabinoid-1 Receptor Antagonist for the Treatment of Obesity", *J. Med. Chem.*, 52, (2009), 2652-2655.
Maggio, B. et al., "Nonclassical *Pschorr* and *Sandmeyer* Reactions in Pyrazole Series", *Helvetica Chimica Acta*, 88. (2005), 2272-2281.
Pauletti, G. M., "Improvement of oral peptide bioavailability: Peptidomimetics and prodrug strategies", *Advanced Drug Delivery Reviews*, 27, (1997), 235-256.

Sellstedt, M., et al., "Syntheis of a Novel Tricyclic Peptidomimetic Scaffold", *Organic Letters*, 10(18), (2008), 4005-4007.
Zhang, X., "Design and synthesis of 6-amino-5-oxo-1, 2, 3, 5-tetrahydro-3-indolizinecarboxylic acids as β-sheet peptidomimetics", *Tetrahedron Letters*, 43, (2002), 9663-9666.
"International Application Serial No. PCT/SE2009/050464, International Preliminary Report on Patentability completed Jul. 20, 2010", 14 pgs.
"International Application Serial No. PCT/SE2009/050464, International Search Report mailed Jul. 16, 2009", 8 pgs.
"International Application Serial No. PCT/SE2009/050464, Written Opinion mailed Jul. 16, 2009", 12 pgs.

* cited by examiner

*Primary Examiner* — Rita Desai
(74) *Attorney, Agent, or Firm* — Schwegman Lundberg & Woessner, P.A.

(57) ABSTRACT

The present invention relates to new compounds of the formula (I), (II), or (III) wherein $R^1$, $R^2$, $R^3$, $R^4$, $R^5$ and W are as defined herein, and pharmaceutical compositions containing them, and their use in the treatment of amyloid diseases, especially Aβ amyloid disease, such as observed in Alzheimer's disease, infectious diseases, PAI-I related disease, and in the manufacture of medicaments for such treatment.

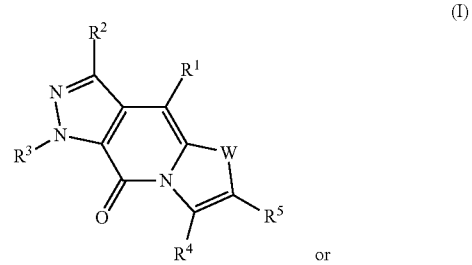

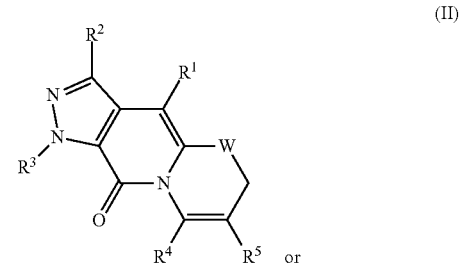

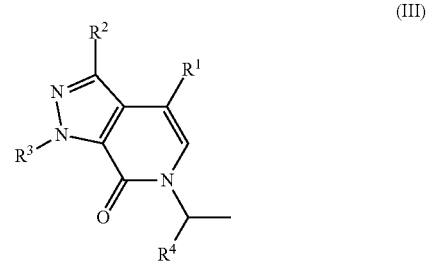

16 Claims, 1 Drawing Sheet

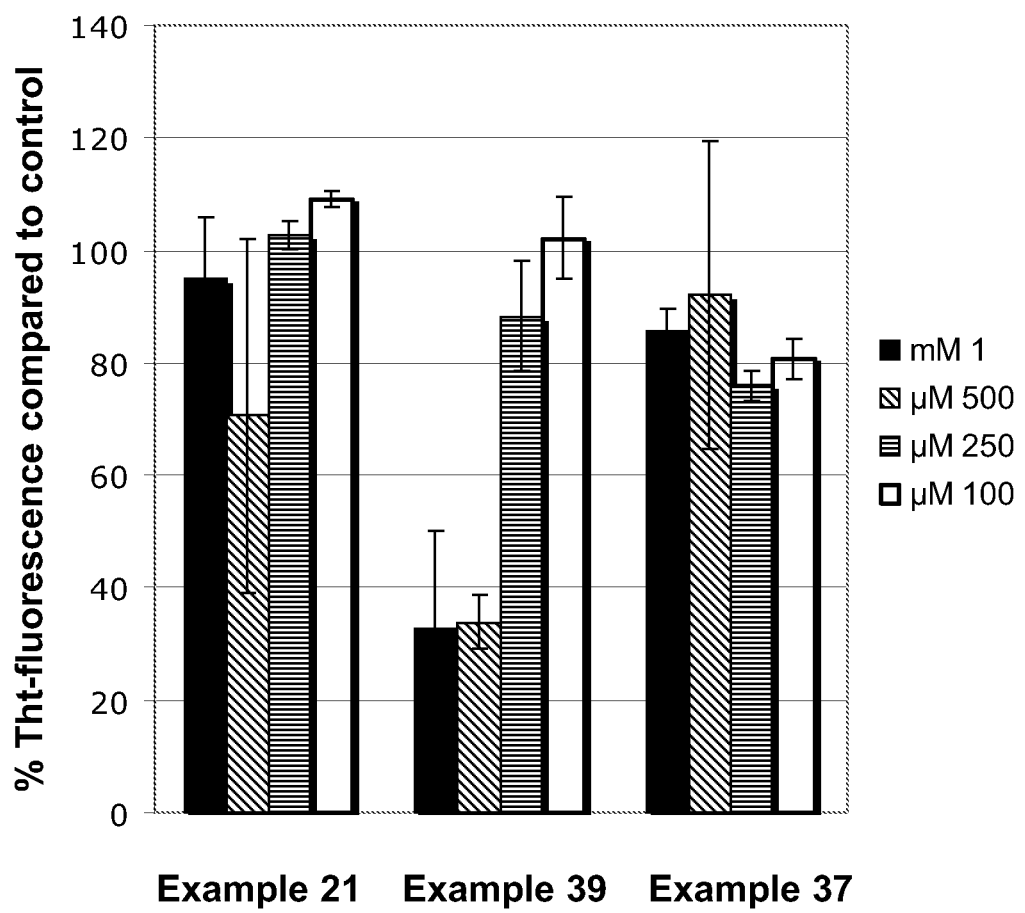

PEPTIDOMIMETIC COMPOUNDS

RELATED APPLICATION

This application is a nationalization under 35 U.S.C. 371 of PCT/SE2009/050464, filed Apr. 30, 2009 and published as WO 2009/134203 A1 on Nov. 5, 2009, which claimed priority under 35 U.S.C. 119(e) to U.S. Provisional Patent Application No. 61/048,976, filed Apr. 30, 2008; which applications and publication are incorporated herein by reference in their entirety.

FIELD OF THE INVENTION

The present invention relates to new compounds of the formula (I), (II), or (III) and pharmaceutical compositions containing them, and their use in the treatment of amyloid diseases, especially Aβ amyloid disease, such as observed in Alzheimer's disease, infectious diseases, PAI-1 related disease, and in the manufacture of medicaments for such treatment.

BACKGROUND OF THE INVENTION

Peptidomimetics compounds can be used to interfere with different protein-protein, peptide-protein and/or peptide-peptide interactions. Such interactions are common mechanisms involved in various natural and disease associated biological processes, including the formation of amyloids, protein folding assisted by chaperones, and interactions between serin proteases and serine protease inhibitors.

Alzheimer's disease is characterized by the accumulation of a 39-43 amino acid peptide termed the β-amyloid protein or Aβ, in a fibrillar form, existing as extracellular amyloid plaques and as amyloid within the walls of cerebral blood vessels. Fibrillar Aβ amyloid deposition in Alzheimer's disease is believed to be detrimental to the patient and eventually leads to toxicity and neuronal cell death, characteristic hallmarks of Alzheimer's disease. Accumulating evidence implicates amyloid, and more specifically, the formation, deposition, accumulation and/or persistence of Aβ fibrils, as a major causative factor of Alzheimer's disease pathogenesis. In addition, besides Alzheimer's disease, a number of other amyloid diseases involve formation, deposition, accumulation and persistence of Aβ fibrils, including Down's syndrome, disorders involving congophilic angiopathy, such as but not limited to, hereditary cerebral hemorrhage of the Dutch type, inclusion body myositosis, dementia pugilistica, cerebral β-amyloid angiopathy, dementia associated with progressive supranuclear palsy, dementia associated with cortical basal degeneration and mild cognitive impairment.

Parkinson's disease is another human disorder characterized by the formation, deposition, accumulation and/or persistence of abnormal fibrillar protein deposits that demonstrate many of the characteristics of amyloid. In Parkinson's disease, an accumulation of cytoplasmic Lewy bodies consisting of filaments of α-synuclein/NAC (non-Aβ component) are believed important in the pathogenesis and as therapeutic targets. New agents or compounds able to inhibit α-synuclein and/or NAC formation, deposition, accumulation and/or persistence, or disrupt pre-formed α-synuclein/NAC fibrils or portions thereof are regarded as potential therapeutics for the treatment of Parkinson's and related synucleinopathies. NAC is a 35 amino acid fragment of α-synuclein that has the ability to form amyloid-like fibrils either in vitro or as observed in the brains of patients with Parkinson's disease. The NAC fragment of α-synuclein is a relative important therapeutic target as this portion of α-synuclein is believed crucial for formation of Lewy bodies as observed in all patients with Parkinson's disease, synucleinopathies and related disorders.

A variety of other human diseases also demonstrate amyloid deposition and usually involve systemic organs (i.e. organs or tissues lying outside the central nervous system), with the amyloid accumulation leading to organ dysfunction or failure. These amyloid diseases (discussed below) leading to marked amyloid accumulation in a number of different organs and tissues, are known as systemic amyloidoses. In other amyloid diseases, single organs may be affected such as the pancreas in 90% of patients with type 2 diabetes. In this type of amyloid disease, the beta-cells in the islets of Langerhans in pancreas are believed to be destroyed by the accumulation of fibrillar amyloid deposits consisting primarily of a protein known as islet amyloid polypeptide (IAPP) Inhibiting or reducing such IAPP amyloid fibril formation, deposition, accumulation and persistence is believed to lead to new effective treatments for type 2 diabetes. In Alzheimer's disease, Parkinson's and "systemic" amyloid diseases, there is currently no cure or effective treatment, and the patient usually dies within 3 to 10 years from disease onset.

The amyloid diseases are classified according to the type of amyloid protein present as well as the underlying disease. Amyloid diseases have a number of common characteristics including each amyloid consisting of a unique type of amyloid protein. The amyloid diseases include, but are not limited to, the amyloid associated with Alzheimer's disease, Down's syndrome, hereditary cerebral hemorrhage with amyloidosis of the Dutch type, dementia pugilistica, inclusion body myositosis (Askanas Ann Neurol 43:521-560, 1993) and mild cognitive impairment (where the specific amyloid is referred to as beta-amyloid protein or Aβ), the amyloid associated with chronic inflammation, various forms of malignancy and Familial Mediterranean Fever (where the specific amyloid is referred to as AA amyloid or inflammation-associated amyloidosis), the amyloid associated with multiple myeloma and other B-cell dyscrasias (where the specific amyloid is referred to as AL amyloid), the amyloid associated with type 2 diabetes (where the specific amyloid protein is referred to as amylin or islet amyloid polypeptide or IAPP), the amyloid associated with the prion diseases including Creutzfeldt-Jakob disease, Gerstmann-Straussler syndrome, kuru and animal scrapie (where the specific amyloid is referred to as PrP amyloid), the amyloid associated with long-term hemodialysis and carpal tunnel syndrome (where the specific amyloid is referred to as α2-microglobulin amyloid), the amyloid associated with senile cardiac amyloidosis and Familial Amyloidotic Polyneuropathy (where the specific amyloid is referred to as transthyretin or prealbumin), and the amyloid associated with endocrine tumors such as medullary carcinoma of the thyroid (where the specific amyloid is referred to as variants of procalcitonin). In addition, the α-synuclein protein which forms amyloid-like fibrils is found as part of Lewy bodies in the brains of patients with Parkinson's disease, Lewy body disease (Lewy in Handbuch der Neurologie, M. Lewandowski, ed., Springer, Berlin pp. 920-933, 1912), multiple system atrophy (Wakabayashi, Acta Neuropath. 96:445-452, 1998), dementia with Lewy bodies, and the Lewy body variant of Alzheimer's disease. For purposes of this disclosure, Parkinson's disease, due to the fact that fibrils develop in the brains of patients with this disease (which contain predominant beta-pleated sheet secondary structure), is now regarded as a disease that also displays the characteristics of an amyloid-like disease.

Systemic amyloid disease which include the amyloid associated with chronic inflammation, various forms of malignancy and familial Mediterranean fever (i.e. AA amyloid or inflammation-associated amyloidosis) (Benson and Cohen, Arth. Rheum. 22:36-42, 1979), and the amyloid associated with multiple myeloma and other B-cell dyscrasias (i.e. AL amyloid) (Harada, J. Histochem. Cytochem. 19:1-15, 1971), as examples, are known to involve amyloid deposition in a variety of different organs and tissues generally lying outside the central nervous system. Amyloid deposition in these diseases may occur, for example, in liver, heart, spleen, gastrointestinal tract, kidney, skin, and/or lungs (Johnson, N. Engl. J. Med. 321:513-518, 1989). For most of these amyloidoses, there is no apparent cure or effective treatment and the consequences of amyloid deposition can be detrimental to the patient. For example, amyloid deposition in the kidney may lead to renal failure, whereas amyloid deposition in the heart may lead to heart failure. For these patients, amyloid accumulation in systemic organs leads to eventual death generally within 3-5 years. Other amyloidoses may affect a single organ or tissue such as observed with the Aβ amyloid deposits found in the brains of patients with Alzheimer's disease and Down's syndrome: the PrP amyloid deposits found in the brains of patients with Creutzfeldt-Jakob disease, Gerstmann-Straussler syndrome, and kuru; the islet amyloid (IAPP) deposits found in the islets of Langerhans in the pancreas of 90% of patients with type 2 diabetes (Johnson, N. Engl. J. Med. 321:513-518, 1989; Lab. Invest. 66:522 535, 1992); the α2-microglobulin amyloid deposits in the medial nerve leading to carpal tunnel syndrome as observed in patients undergoing long-term hemodialysis (Geyjo, Biochem. Biophys. Res. Comm. 129:701-706, 1985); the prealbumin/transthyretin amyloid observed in the hearts of patients with senile cardiac amyloid; and the prealbumin/transthyretin amyloid observed in peripheral nerves of patients who have familial amyloidotic polyneuropathy (Skinner and Cohen, Biochem. Biophys. Res. Comm. 99:1326-1332, 1981).

Chaperones are essential for the assembly of adhesive protein organelles known as pili or fimbriae present on the surface of bacteria, in absence of these organelles the bacteria become non-infectious Mulvey, Cellular Microbiology, 4:257-271, 2002). Thus, compounds interfering with pili/fimbriae formation, pilicides, represent a novel class of antibacterial agents directed against bacterial virulence (Lee, Current Opinion in Pharmacology, 3: 513-519, 2003). The compounds of this invention can acts as inhibitors of pili and/or fibriae formation of Gram negative bacteria and can be used for the treatment, prevention and/or prophylaxis of infectious diseases caused by Gram-negative bacteria. The disease to be treated can be selected from infectious disease caused by a Gram-negative bacterium selected from the group consisting of *Escherichia coli, Heamophilus influenza, Salmonella enteriditis, Salmonella typhimurium, Bordetellapertussis, Yersiniapestis, Yersinia enterocolitica, Helicobacter pylori* and *Klebsiella pneumoniae*.

The serine protease PAI-1 (plasminogen activator inhibitor type 1) is one of the primary inhibitors of the fibrinolytic system. Fibrinolysis is the result of a series of enzymatic reactions resulting in the degradation of fibrin by plasmin. The activation of plasminogen is the central process in fibrinolysis. The cleavage of plasminogen to produce plasmin is accomplished by the plasminogen activators, tissue-type plasminogen activator (t-PA) or urokinase-type plasminogen activator (u-PA). The fibrinolytic system is not only responsible for the removal of fibrin from circulation but is also involved in several other biological processes including ovulation, embryogenesis, intima proliferation, angiogenesis, tumorigenesis, atherosclerosis, and Alzheimer's disease.

Elevated levels of PAI-1, due to increased production or activity, have been seen associated with a variety of diseases and conditions including those associated with impairment of fibrinolysis. These diseases and conditions include, but are not limited to, thrombosis, coronary heart disease, renal fibrosis, atherosclerotic plaque formation, pulmonary disease, myocardial ischemia, atrial fibrillation, coagulation syndromes, thromboembolic complications of surgery, peripheral arterial occlusion and pulmonary fibrosis. Other disorders include, but are not limited to, cancer, polycystic ovary syndrome, diabetes, and obesity.

For example, elevated levels of PAI-1 have been implicated in thrombotic diseases, e.g., diseases characterized by formation of a thrombus that obstructs vascular blood flow locally that detaches and embolizes to occlude blood flow downstream (Krishnamurti, Blood, 69,798 (1987); Reilly, Arteriosclerosis and Thrombosis, 11, 1276, (1991); Carmeliet, Journal of Clinical Investigation, 92, 2756 (1993); Rocha, Fibrinolysis, 8, 294, 1994; Aznar, Haemostasis, 24, 243 (1994)). A Fab-fragment of a PAI-1 inhibiting antibody enhances fibrinolysis impaired in rats given endotoxin, leading to decreased tissue fibrin deposition (Abrahamsson, Thrombosis and Haemostasis, 75, 118 (1996).

Elevated PAI-1 levels have also been implicated in diseases such as polycystic ovary syndrome (Nordt, Journal of Clinical Endocrinology and Metabolism, 85, 4, 1563 (2000)), bone loss due to estrogen deficiency (Daci, Journal of Bone and Mineral Research, 15, 8, 1510 (2000)), cystic fibrosis, idiopathic pulmonary fibrosis, diabetes, chronic peridontitis, lymphomas, diseases associated with extracellular matrix accumulation, malignancies, diseases associated with neoangiogenesis, inflammatory diseases, vascular damage associated with infections, and diseases associated with increased levels such as breast and ovarian cancer.

The compounds of the invention are inhibitors of PAI-1 either as such or, in the case of prodrugs, after administration. The compounds of the invention are thus expected to be useful in PAI-1 related disorders, such as in the treatment or prophylaxis of thrombosis and hypercoagulability in blood and tissues of mammals, including man.

It is known that hypercoagulability may lead to thromboembolic diseases. Conditions associated with hypercoagulability and thrombo-embolic diseases which may be mentioned include protein C resistance and inherited or acquired deficiencies in antithrombin III, protein C, protein S and heparin cofactor II. Other conditions known to be associated with hyper-coagulability and thrombo-embolic disease include circulatory and septic shock, circulating antiphospholipid antibodies, homocysteinaemia, heparin induced thrombocytopenia and defects in fibrinolysis. The compounds of the invention are thus indicated both in the therapeutic and/or prophylactic treatment of conditions mentioned in this application.

Particular disease states which may be treated according to the present invention include venous thrombosis and pulmonary embolism, arterial thrombosis (e.g. in myocardial infarction, unstable angina, ischemic stroke and peripheral arterial thrombosis) and systemic embolism usually from the atrium during atrial fibrillation or from the left ventricle after transmural myocardial infarction.

Further indications include the therapeutic and/or prophylactic treatment of disseminated intravascular coagulation caused by bacteria, multiple trauma, intoxication or any other mechanism, fibrinolytic treatment when blood is in contact with foreign surfaces in the body, such as vascular grafts, vascular stents, vascular catheters, mechanical and biological prosthetic valves or any other medical device, and fibrinolytic treatment when blood is in contact with medical devices outside the body, such as during cardiovascular surgery using a heart-lung machine or in haemodialysis.

The compounds of the invention may also be combined and/or coadministered with any antithrombotic agent with a different mechanism of action, such as the antiplatelet agents acetylsalicylic acid, ticlopidine, clopidogrel, thromboxane receptor and/or synthetase inhibitors, fibrinogen receptor antagonists, prostacyclin mimetics, phosphodiesterase inhibitors, ADP-receptor ($P_2T$) antagonists, carboxypeptidase U inhibitors and thrombin inhibitors.

The compounds of the invention may further be combined and/or coadministered with thrombolytics such as tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction and stroke.

WO 01/36426, in the name of Washington University, discloses pyridones in treating or preventing Gram-negative bacterial infections.

Almqvist et al., J. Org. Chem. 2007, 72, 4917-4924 discloses diverse functionalization of thiazolo ring-fused 2-pyridones.

JP2005320346, WO 2005030716 and WO 200174793 all disclose PAI-1 inhibitors.

DESCRIPTION OF THE INVENTION

One object of the present invention is a compound of the formula (I), (II) or (III):

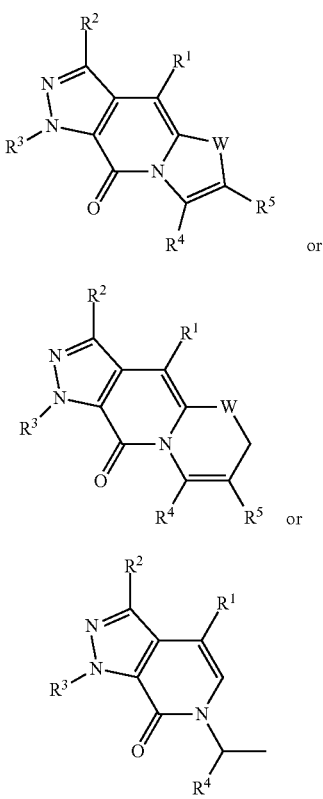

and pharmaceutically acceptable salts, prodrugs and enantiomers thereof, wherein W is selected from S, SO, $SO_2$, O, P, PO, $PO_2$, $CH_2$, $NR^1$, $NC(O)R^1$, and $NSO_2R^1$;

$R^1$ comprises $(CH_2)_m D$ wherein m is a natural number being 0, 1, 2, 3, 4, or 5 and D comprises hydrogen, unsubstituted or substituted alkyl, unsubstituted or substituted alkenyl, unsubstituted or substituted alkynyl, unsubstituted or substituted cycloalkyl, unsubstituted or substituted aryl, unsubstituted or substituted heteroaryl;

$R^2$ comprises $(CH_2)_n A$ wherein n is a natural number being 0, 1, 2, 3, 4, or 5 and A comprises hydrogen, unsubstituted or substituted alkyl, unsubstituted or substituted alkenyl, unsubstituted or substituted alkynyl, unsubstituted or substituted cycloalkyl, unsubstituted or substituted aryl, unsubstituted or substituted aryloxy, unsubstituted or substituted heteroaryl;

$R^3$ comprises $(CH_2)_n A$ wherein n is a natural number being 0, 1, 2, 3, 4, or 5 and A comprises hydrogen, unsubstituted or substituted alkyl, unsubstituted or substituted alkenyl, unsubstituted or substituted alkynyl, unsubstituted or substituted cycloalkyl, unsubstituted or substituted aryl, unsubstituted or substituted heteroaryl;

$R^4$ comprises $CO_2Y$, $B(OY)_2$, CHO, $CH_2OY$, $CH(CO_2Y)_2$, $PO(OY)_2$ wherein Y comprises hydrogen, unsubstituted or substituted alkyl, unsubstituted or substituted alkenyl, unsubstituted or substituted alkynyl, unsubstituted or substituted cycloalkyl, unsubstituted or substituted aryl, unsubstituted or substituted heteroaryl; or $R^4$ comprises tetrazolyl; or $R^4$ comprises CONHZ wherein Z comprises hydrogen, hydroxy, alkyl, alkylsulfonyl, arylsulfonyl or cyanoalkyl;

$R^5$ comprises hydrogen, unsubstituted or substituted alkyl, unsubstituted or substituted alkoxy, unsubstituted or substituted aryl, unsubstituted or substituted heteroaryl.

For Formulas (I) and (II), it should be noted that the bond between the carbon atom bonded to $R^4$ and the carbon atom bonded to $R^5$ may either be a single bond or a double bond.

In another embodiment there is provided a compound of the formula (I) or (III), wherein W is selected from S, SO, $SO_2$, O, $CH_2$, $NC(O)R^6$, and $NSO_2R^6$;

$R^1$ is $(CH_2)_m D$ wherein m is 0 and D is selected from unsubstituted or substituted cycloalkyl, unsubstituted or substituted aryl, and unsubstituted or substituted heteroaryl;

$R^2$ comprises $(CH_2)_n A$ wherein n is a natural number being 0, 1, 2, 3, 4, or 5 and A comprises hydrogen, unsubstituted or substituted alkyl, unsubstituted or substituted cycloalkyl, unsubstituted or substituted aryl, unsubstituted or substituted aryloxy, unsubstituted or substituted heteroaryl;

$R^3$ comprises $(CH_2)_n A$ wherein n is a natural number being 0, 1, 2, 3, 4, or 5 and A comprises hydrogen, unsubstituted or substituted alkyl;

$R^4$ is selected from $CO_2Y$ wherein Y is selected from hydrogen or alkyl; tetrazolyl; and CONHZ wherein Z is selected from hydrogen, hydroxy, alkyl, alkylsulfonyl, arylsulfonyl, and cyanoalkyl;

$R^5$ is selected from hydrogen, unsubstituted or substituted alkyl, unsubstituted or substituted alkoxy, unsubstituted or substituted aryl, unsubstituted or substituted heteroaryl;

$R^6$ is selected from hydrogen, alkyl and aryl.

In another embodiment there is provided a compound of the formula (I) or (III), wherein W is selected from S and $SO_2$;

$R^1$ is $(CH_2)_m D$ wherein m is 0 and D is selected from unsubstituted or substituted cycloalkyl, unsubstituted or substituted aryl, and unsubstituted or substituted heteroaryl;

$R^2$ comprises $(CH_2)_nA$ wherein n is a natural number being 0, 1, 2, 3, 4, or 5 and A comprises hydrogen, unsubstituted or substituted alkyl, unsubstituted or substituted aryl, unsubstituted or substituted aryloxy, unsubstituted or substituted heteroaryl;

$R^3$ comprises $(CH_2)_nA$ wherein n is a natural number being 0, 1, 2, 3, 4, or 5 and A comprises hydrogen, unsubstituted or substituted alkyl;

$R^4$ is selected from $CO_2Y$ wherein Y is selected from hydrogen or alkyl; tetrazolyl; and CONHZ wherein Z is selected from hydrogen, hydroxy, alkyl, alkylsulfonyl, arylsulfonyl, and cyanoalkyl;

$R^5$ is selected from hydrogen, alkyl, alkoxy, unsubstituted or substituted aryl, unsubstituted or substituted heteroaryl.

In another embodiment there is provided a compound of the formula (I) or (III), wherein W is S;

$R^1$ is $(CH_2)_mD$ wherein m is 0 and D is selected from unsubstituted or substituted cycloalkyl, unsubstituted or substituted aryl;

$R^4$ is selected from $CO_2Y$ wherein Y is selected from hydrogen; tetrazolyl; and CONHZ wherein Z is selected from alkylsulfonyl and arylsulfonyl;

$R^5$ is selected from hydrogen, methyl, methoxy, and phenyl.

In another embodiment, aryl is $C_{6-15}$ aryl, aryloxy is $C_{6-15}$ aryloxy, alkenyl is $C_{1-15}$ alkenyl, alkynyl is $C_{1-15}$ alkynyl, cycloalkyl is $C_{3-6}$ alkyl, and heteroaryl is $C_{5-15}$ heteroaryl.

In another embodiment, substituted aryl is aryl substituted by one or more halogens, especially fluoro.

In another embodiment, substituted aryl is aryl substituted by one or more haloalkyl, especially trifluoromethyl.

In another embodiment, substituted aryl is aryl substituted by one or more fluoro.

In another embodiment, substituted aryl is aryl substituted by one or more methoxy.

In another embodiment, the stereochemical configuration around the carbon which is covalently bound to $R_4$ is (R).

In another embodiment, the stereochemical configuration around the carbon which is covalently bound to $R_4$ is (S).

Specific compounds are denoted in Examples 21-25, and 27-42.

Another object of the present invention is a process for the preparation of a compound above comprising reacting a compound of formula (I) with Raney® nickel to give a compound of formula (III).

DEFINITIONS

As used herein, alkyl means an alkyl group being straight or branched having from 1 to 10 carbon atoms. Examples include methyl, ethyl, propyl, isopropyl, butyl, hexyl, heptyl, octyl, nonyl, decyl and the like. The alkyl groups may be unsubstituted or substituted.

As used herein, alkoxy means an alkoxy group being straight or branched having from 1 to 10 carbon atoms. Examples include methoxy, ethoxy, propoxy, isopropoxy, butoxy, hexoxy, heptoxy, octoxy, nonoxy, decoxy and the like. The alkoxy groups may be unsubstituted or substituted.

As used herein, alkenyl means an alkenyl group being straight or branched having from 2 to 10 carbon atoms. Examples include ethenyl, propenyl, isopropenyl, butenyl, hexenyl, heptyl, heptenyl, octenyl, nonenyl, docenyl and the like. The alkenyl groups may be unsubstituted or substituted.

As used herein, alkynyl means an alkynyl group being straight or branched having from 2 to 10 carbon atoms. Examples include ethynyl, propynyl, butynyl, hexynyl, heptynyl, octynyl, nonynyl, decynyl and the like. The alkynyl groups may be unsubstituted or substituted.

As used herein, cycloalkyl means a cycloalkyl group being straight or branched having from 3 to 10 carbon atoms. Examples include cyclopropyl, cyclobutyl, cyclopentyl, cyclohexyl, cycloheptyl, cyclooctyl, cyclononyl, cyclodecyl and the like. The cycloalkyl groups may be unsubstituted or substituted.

As used herein, acyl means an acyl group being straight or branched having from 1 to 10 carbon atoms. Examples include formyl, acetyl, propionyl, isopropionyl, butyryl, hexanoyl, heptanoyl, octanoyl, nonanoyl, decanoyl and the like. The acyl groups may be unsubstituted or substituted.

The aryl moieties described here, either alone or with various substituents, contain from 6 to 15 carbon atoms and include phenyl, 1-naphthalenyl and 2-naphthalenyl. Substituents include alkoxy, halogen, hydroxyl, alkyl, aryl, alkenyl, acyl, acyloxy, nitro, amino, amido, trifluoromethyl, etc.

The aryloxy moieties described here, either alone or with various substituents, contain from 6 to 15 carbon atoms and include phenoxy, 1-naphthalenoxy and 2-naphthalenoxy. Substituents include alkoxy, halogen, hydroxyl, alkyl, aryl, alkenyl, acyl, acyloxy, nitro, amino, amido, trifluoromethyl, etc.

The heteroaryl moieties described here, either alone or with various substituents, contain from 3 to 15 carbon atoms and include furans, thiophenes, indoles, furyl, pyridyl, thienyl, tryptophane and the like. Substituents include alkanoxy, halogen, hydroxyl, alkyl, aryl, alkenyl, acyl, acyloxy, nitro, amino, amido, trifluoromethyl, etc.

The substituents of the substituted alkyl, alkoxy, alkenyl, alkynyl, cycloalkyl, acyl, aryl, aryloxy, and heteroaryl groups and moieties described herein, may be hydroxy, halogen, alkyl, alkenyl, alkynyl, aryl, heteroaryl and/or may contain nitrogen, oxygen, sulfur, halogens and include, for example, lower alkoxy such as methoxy, ethoxy, butoxy, halogen such as chloro or fluoro, nitro, amino, keto, and trifluoromethyl.

In another embodiment, the substituents of the substituted alkyl, alkoxy, alkenyl, alkynyl, cycloalkyl, acyl, aryl, aryloxy, and heteroaryl groups and moieties described herein, may be hydroxy, halogen, alkyl, alkenyl, alkynyl, aryl, heteroaryl, and trifluoromethyl.

As used herein, the term "halogen" denotes a fluoro, chloro, bromo, or iodo group. The term "perhalo" denotes a group having the highest possible number of halogen atoms bonded thereto.

As used herein, the term "haloalkyl" denotes an alkyl group substituted by one or more halogens. Examples of haloalkyl are chloromethyl, trichloromethyl, and trifluoromethyl.

As used herein, when two or more groups are used in connection with each other, it means that each group is substituted by the immediately preceding group. For instance, trifluoromethylphenyl means a phenyl group substituted by a trifluoromethyl group.

As used herein, the terms "prevent" or "prevention" and prophylaxis are given their ordinary meaning and thus means the avoidance or alleviation of the serious consequences of a disease or a side-effect by early detection.

As used herein, the term "mammal" means a human or an animal such as monkeys, primates, dogs, cats, horses, cows, etc.

As used herein, the term "PAI-1 related disorder or disease" refers to any disease or condition that is associated with increased or enhanced expression or activity of PAI-1 or increased or enhanced expression or activity of a gene encoding PAI-1. The term "PAI-1 related disorder or disease" also refers to any disease or condition wherein inhibition of PAI-1 is beneficial.

As used herein, the single enantiomers, racemic mixtures and unequal mixtures of two enantiomers are within the scope of the invention, where such isomers exist. It should be understood that all the diastereomeric forms possible (pure enantiomers, racemic mixtures and unequal mixtures of two or more diastereomers), tautomers, and atropisomers are within the scope of the invention.

As used herein, the term "pharmaceutically acceptable salts" includes acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo or by freeze-drying). Salts may also be prepared by exchanging a counter-ion of a compound of the invention in the form of a salt with another counter-ion using a suitable ion exchange resin.

As used herein the term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Suitable acids are non-toxic and include e g, but are not limited to, hydrochloric acid, hydrobromic acid, hydroiodic acid, sulphuric acid, nitric acid, acetic acid, citric acid, ascorbic acid, lactic acid, malic acid, and tartaric acid. Suitable bases are non-toxic and include e g, but are not limited to, sodium hydroxide, potassium hydroxide, lithium hydroxide, ammonia, methylamine, dimethylamine, trimethylamine, and triethylamine.

In the context of the present specification, the term "treat" also includes "prophylaxis" unless there are specific indications to the contrary. The term "treat" within the context of the present invention further encompasses to administer an effective amount of a compound of the present invention, to mitigate either a pre-existing disease state, acute or chronic, or a recurring condition. This definition also encompasses prophylactic therapies for prevention of recurring condition and continued therapy for chronic disorders.

The compounds of the present invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints.

In one embodiment of the present invention, the route of administration may be oral, intravenous or intramuscular.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of the present invention, inert, pharmaceutically acceptable carriers can be either solid or liquid. Solid form preparations include powders, tablets, dispersable granules, capsules, cachets, and suppositories.

A solid carrier can be one or more substances, which may also act as diluents, flavouring agents, solubilizers, lubricants, suspending agents, binders, or tablet disintegrating agents; it can also be an encapsulating material.

In powders, the carrier is a finely divided solid, which is in mixture with the finely divided compound of the present invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogenous mixture is then poured into conveniently sized moulds and allowed to cool and solidify.

Suitable carriers are magnesium carbonate, magnesium stearate, talc, lactose, sugar, pectin, dextrin, starch, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavouring agents, stabilizers, and thickening agents as desired. Aqueous solutions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will according to one embodiment of the present invention include 0.05% to 99% weight (percent by weight), according to an alternative embodiment from 0.10 to 50% weight, of the compound of the present invention, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skills in the art.

The above-mentioned subject-matter for a pharmaceutical composition comprising a compound according to the present invention is applied analogously for a pharmaceutical composition comprising a combination according to the present invention.

Another object of the present invention is a compound as disclosed above for use in medicine.

Another object of the present invention is a pharmaceutical formulation comprising a compound as disclosed above in admixture with pharmaceutically acceptable adjuvants, diluents and/or carriers.

According to another aspect of the present invention, there is provided a compound as disclosed above for use in the treatment, prevention and/or prophylaxis of amyloid diseases. Amyloid diseases suitable for treatment with the compounds of this invention are diseases associated with the formation, deposition, accumulation, or persistence of amyloid fibrils, especially the fibrils of an amyloid protein selected from the group consisting of Aβ amyloid, AA amyloid, AL amyloid, IAPP amyloid, PrP amyloid, α2-microglobulin amyloid, transthyretin, prealbumin, and procalcitonin, especially Aβ amyloid and IAPP amyloid. Suitable such diseases include Alzheimer's disease, Down's syndrome, dementia pugilistica, multiple system atrophy, inclusion body myositosis, hereditary cerebral hemorrhage with amyloidosis of the Dutch type, Nieman-Pick disease type C, cerebral β-amyloid angiopathy, dementia associated with cortical basal degeneration, the amyloidosis of type 2 diabetes, the amyloidosis of chronic inflammation, the amyloidosis of malignancy and Familial Mediterranean Fever, the amyloidosis of multiple myeloma and B-cell dyscrasias, the amyloidosis of the prion diseases, Creutzfeldt-Jakob disease, Gerstmann-Straussler syndrome, kuru, scrapie, the amyloidosis associated with carpal tunnel syndrome, senile cardiac amyloidosis, familial amyloidotic polyneuropathy, and the amyloidosis associated with endocrine tumors, especially Alzheimer's disease and type 2 diabetes.

The compounds also act to inhibit or prevent α-synuclein/NAC fibril formation, inhibit or prevent α-synuclein/NAC fibril growth, and/or cause disassembly, disruption, and/or disaggregation of preformed α-synuclein/NAC fibrils and α-synuclein/NAC-associated protein deposits.

According to another aspect of the present invention, there is provided a compound as disclosed above for use in the treatment, prevention and/or prophylaxis of "Synuclein diseases" or "synucleinopathies" suitable for treatment with the compounds of this invention are diseases associated with the formation, deposition, accumulation, or persistence of synuclein fibrils, especially α-synuclein fibrils. Suitable such diseases include Parkinson's disease, familial Parkinson's disease, Lewy body disease, the Lewy body variant of Alzheimer's disease, dementia with Lewy bodies, multiple system atrophy, and the Parkinsonism-dementia complex of Guam.

The compounds according to the invention can also act as antibacterial agents, by inhibiting pilus formation in Gram-negative bacteria.

According to another aspect of the present invention, there is provided a compound as disclosed above for use in the treatment, prevention and/or prophylaxis of infectious diseases caused by Gram-negative bacteria. The disease to be treated can be selected from infectious diseases caused by a Gram-negative bacterium selected from the group consisting of *Escherichia coli, Heamophilus influenza, Salmonella enteriditis, Salmonella typhimurium, Bordetellapertussis, Yersiniapestis, Yersinia enterocolitica, Helicobacter pylori* and *Klebsiella pneumoniae.*

According to another aspect of present invention, there is provided a compound as disclosed above for use in the treatment of a disorder wherein inhibition of PAI-1 may be beneficial, which disorder is selected from thrombosis, coronary heart disease, renal fibrosis, atherosclerotic plaque formation, pulmonary disease, myocardial ischemia, atrial fibrillation, coagulation syndromes, thromboembolic complications of surgery, peripheral arterial occlusion, pulmonary fibrosis, cancer, polycystic ovary syndrome, diabetes, obesity, and Alzheimer's disease.

Another object of the present invention is the use of a compound above, in the manufacture of a medicament for treating a disorder wherein inhibition of PAI-1 may be beneficial, which disorder is selected from thrombosis, coronary heart disease, renal fibrosis, atherosclerotic plaque formation, pulmonary disease, myocardial ischemia, atrial fibrillation, coagulation syndromes, thromboembolic complications of surgery, peripheral arterial occlusion, pulmonary fibrosis, cancer, polycystic ovary syndrome, diabetes, obesity, and Alzheimer's disease.

In another embodiment the compound is combined and/or coadministered with another antithrombotic agent.

Another object of the present invention is a method for treating a disorder wherein inhibition of PAI-1 may be beneficial, which disorder is selected from thrombosis, coronary heart disease, renal fibrosis, atherosclerotic plaque formation, pulmonary disease, myocardial ischemia, atrial fibrillation, coagulation syndromes, thromboembolic complications of surgery, peripheral arterial occlusion, pulmonary fibrosis, cancer, polycystic ovary syndrome, diabetes, obesity, and Alzheimer's disease, by administering to a mammal of a compound above.

In another embodiment the compound is combined and/or coadministered with another antithrombotic agent.

In the following, the present invention is illuminated by the following non-limiting Examples.

When used, the expressions "comprise" and "comprising" denote "include" and "including" but not limited to. Thus, other ingredients, carriers and additives may be present.

DESCRIPTION OF DRAWINGS

FIG. 1. Amyloid Aggregation Assay

Effect of test substances on aggregation of Aβ 1-40 was measured by detecting fluorescence of added Thioflavin T (ThT). The ThT-fluorescence of Aβ 1-40 aggregated in the presence of the indicated substances was compared to the ThT-fluorescence of Aβ 1-40 aggregated in the presence of 5% DMSO.

EXAMPLES

Abbreviations

DEAD=diethyl azodicarboxylate
rt or RT—room temperature
TFA=trifluoroacetic acid
THF=tetrahydrofuran
t—triplet
s—singlet
d—doublet
q—quartet
quint—quintet m—multiplet
br—broad
bs—broad singlet
dm—doublet of multiplet
bt—broad triplet
dd—doublet of doublet General Synthesis:

All reactions were carried out under an inert atmosphere with dry solvents under anhydrous conditions, unless otherwise stated. Zn (dust) was activated by stirring it in 10% HCl for two minutes. It was then filtered, washed with water and acetone and dried under vacuum. TLC was performed on Silica Gel 60 $F_{254}$ (Merck) using UV light detection. Flash column chromatography (eluents given in brackets) employed normal phase silica gel (Matrex, 60 Å, 35-70 µm, Grace Amicon). Optical rotations were measured with a Perkin-Elmer 343 polarimeter at 20° C. and 589 nm. The $^1$H and $^{13}$C NMR spectra were recorded at 298 K with a Bruker DRX-400 spectrometer in $CDCl_3$ with residual $CHCl_3$ ($\delta_H$ 7.26 ppm) or $CDCl_3$ ($\delta_C$ 77.16 ppm) as internal standard, or in MeOH-$d_4$ with residual $CD_2HOD$ ($\delta_H$ 3.31 ppm) or $CD_3OD$ ($\delta_C$ 49.0 ppm) as internal standard.

Pyridones of general structure IV was prepared in analogy with previously published procedures in *J. Org. Chem.* 2001, 66(20), 6756-6761.

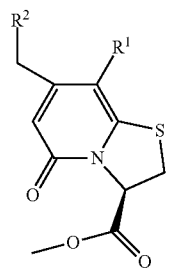

IV

In the following table, the structural formulas for Examples 1-5 and 30-31 are denoted—all being of Formula IV.

| Example | R¹ | R² |
|---|---|---|
| 1 | 3-trifluoromethylphenyl | isobutyl |
| 2 | 3-trifluoromethylphenyl | n-propyl |
| 3 | 3-trifluoromethylphenyl | n-pentyl |
| 4 | 3-trifluoromethylphenyl | hydrogen |
| 5 | 3-trifluoromethylphenyl | n-hexyl |
| 30 | phenyl | hydrogen |
| 31 | phenyl | isobutyl |

General Procedure for Nitration (V)

A flask was charged with pyridone of general structure IV and $NaNO_2$ (1.05 equiv.). $CH_2Cl_2$ (30 ml/mmol IV) was added. A balloon filled with $O_2(g)$ was connected through a rubber septum and TFA (1.15 ml/mmol IV) was added drop-wise while stirring. The mixture was stirred at room temperature over night and then neutralized by addition of $NaHCO_3$ (sat., aq.). The organic phase was separated and the aqueous phase was extracted with $CH_2Cl_2$. The combined organic phases were dried over $NaSO_4(s)$, filtered and then concentrated under reduced pressure. The crude product was purified with silica gel chromatography using heptane:ethyl acetate (4:1→1:2) as eluent, yielding V.

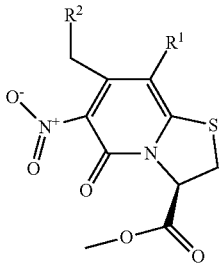

V

In the following table, the structural formulas for Examples 6-10 are denoted—all being of Formula V.

| Example | R¹ | R² |
|---|---|---|
| 6 | 3-trifluoromethylphenyl | isobutyl |
| 7 | 3-trifluoromethylphenyl | n-propyl |
| 8 | 3-trifluoromethylphenyl | n-pentyl |
| 9 | 3-trifluoromethylphenyl | hydrogen |
| 10 | 3-trifluoromethylphenyl | n-hexyl |

General Procedure for Reduction (VI):

Nitro product of general structure V was dissolved in acetic acid (7 ml/mmol V). Zn(dust) (5 equiv.) was added in portions and the mixture was then stirred at rt for 4 h. The mixture was filtered through a layer of Celite® and then concentrated under reduced pressure. The residue was dissolved in $CH_2Cl_2$ and washed with $NaHCO_3$ (sat., aq.). The aqueous layer was extracted with $CH_2Cl_2$ and the combined organic phases were then dried over $NaSO_4(s)$, filtered and concentrated under reduced pressure. The crude product was purified with silica gel chromatography using heptane:ethyl acetate (1:2→1:4) as eluent, yielding VI.

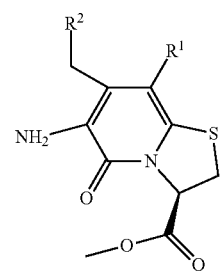

VI

In the following table, the structural formulas for Examples 11-15 and 32-33 are denoted—all being of Formula VI.

| Example | R¹ | R² |
|---|---|---|
| 11 | 3-trifluoromethylphenyl | isobutyl |
| 12 | 3-trifluoromethylphenyl | n-propyl |
| 13 | 3-trifluoromethylphenyl | n-pentyl |
| 14 | 3-trifluoromethylphenyl | hydrogen |
| 15 | 3-trifluoromethylphenyl | n-hexyl |
| 32 | phenyl | hydrogen |
| 33 | phenyl | isobutyl |

General Procedure for Pyrazole Formation (VII):

Amine of general structure VI was dissolved in acetic acid (110 ml/mmol VI). 0.2M $NaNO_2$ (aq.) (5.0 ml/mmol VI) was added drop-wise over 20 min while stirring at rt. The mixture was stirred additional one hour before addition of water (200 ml/mmol VI) and then lyophilized. The residue was taken up in $CH_2Cl_2$ and washed with $NaHCO_3$ (sat., aq.). The aqueous phase was extracted with $CH_2Cl_2$ and the combined organic phases were dried over $NaSO_4$(s), filtered and concentrated under reduced pressure. The crude product was purified with silica gel chromatography using heptane:ethyl acetate:methanol (100:100:1→50:50:1) as eluent. The product was dissolved in methanol and Amberlite® IR-120 ($H^+$) (approx. 4 ml/mmol VI) was added. The mixture was stirred for 5 min before the resin was filtered off and washed with methanol. The filtrate was concentrated under reduced pressure to yield VII.

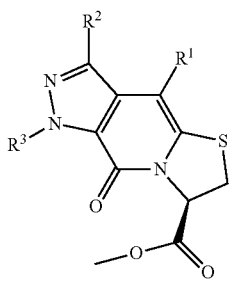

VII

In the following table, the structural formulas for Examples 16-20, 26, and 34-36 are denoted—all being of Formula VII.

| Example | $R^1$ | $R^2$ | $R^3$ |
|---|---|---|---|
| 16 | 3-trifluoromethylphenyl | isobutyl | hydrogen |
| 17 | 3-trifluoromethylphenyl | n-propyl | hydrogen |
| 18 | 3-trifluoromethylphenyl | n-pentyl | hydrogen |
| 19 | 3-trifluoromethylphenyl | hydrogen | hydrogen |
| 20 | 3-trifluoromethylphenyl | n-hexyl | hydrogen |
| 26 | 3-trifluoromethylphenyl | isobutyl | ethyl |
| 34 | phenyl | hydrogen | hydrogen |
| 35 | phenyl | isobutyl | hydrogen |
| 36 | phenyl | bromine | hydrogen |

General Procedure for Hydrolysis (VIII):

Pyrazole of general structure VII was dissolved in THF:methanol 3:7 (20 ml/mmol VII). 0.1 M LiOH (aq.) (1.0 ml/mmol) was added drop-wise at 0° C. The ice-bath was removed and the mixture was stirred over night at rt. If necessary additional 0.1 M LiOH (aq.) was added the mixture was stirred another 6 h before concentration under reduced pressure. The residue was dissolved in methanol and Amberlite® IR-120 ($H^+$) (approx. 7 ml/mmol VII) was added. The mixture was stirred for 5 min before the resin was filtered off and washed with methanol. The filtrate was concentrated under reduced pressure to yield VIII.

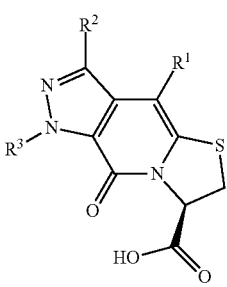

VIII

In the following table, the structural formulas for Examples 21-25, 27-28, and 37 are denoted—all being of Formula VIII.

| Example | $R^1$ | $R^2$ | $R^3$ |
|---|---|---|---|
| 21 | 3-trifluoromethylphenyl | isobutyl | hydrogen |
| 22 | 3-trifluoromethylphenyl | n-propyl | hydrogen |
| 23 | 3-trifluoromethylphenyl | n-pentyl | hydrogen |
| 24 | 3-trifluoromethylphenyl | hydrogen | hydrogen |
| 25 | 3-trifluoromethylphenyl | n-hexyl | hydrogen |
| 27 | 3-trifluoromethylphenyl | isobutyl | ethyl |
| 28 | 3,4-difluorophenyl | n-hexyl | hydrogen |
| 37 | phenyl | isobutyl | hydrogen |

Example 29 is the corresponding phenylsulfonamide of Example 28.

General Procedure for Suzuki Coupling of Compound E to Produce IX 3.6 ml methanol was added to 73 mg (0.18 mmol) of compound E, 4.0 mg (0.018 mmol) $Pd(OAc)_2$, 11 mg (0.018 mmol) rac-BINAP, 20 mg (0.34 mmol) KF, and 0.36 mmol (2.0 equiv.) of the boronic acid to be coupled. The mixture was heated with micro waves in a sealed tube at 50° C. for 3 min and then at 140° C. for 20 min. (Compound 10e was heated additional 40 min at 140° C.) The resulting mixture was concentrated under reduced pressure. The residue was taken up in a small amount of pyridine and then passed through a silica gel column using toluene: MeCN:pyridine 95:5:2→90:10:2 as eluent. After concentration under reduced pressure the residue was dissolved in 3.6 ml methanol:pyridine 3:1 and 1.8 ml 0.1 M LiOH (aq.) was added. The solution was stirred at rt over night. Additional 0.9 ml 0.1 M LiOH (aq.) was added and the reaction was stirred another 6-7 h before concentration under reduced pressure. The crude product was dissolved in $HCO_2H$:DMSO 1:1 and purified with preparative HPLC using a C8-column. Methanol:water with 1% formic acid added was used as mobile phase. After purification, methanol was removed under reduced pressure and the residue was lyophilized from 5% aqueous acetic acid affording IX as powder.

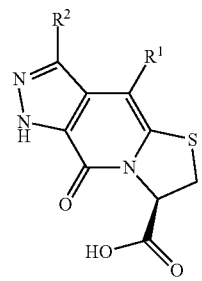

IX

In the following table, the structural formulas for Examples 38-42 are denoted—all being of Formula IX.

| Example | $R^1$ | $R^2$ |
|---|---|---|
| 38 | phenyl | phenyl |
| 39 | phenyl | 4-metoxyphenylphenyl |
| 40 | phenyl | 3-nitrophenyl |
| 41 | phenyl | 3-furyl |
| 42 | phenyl | 2-tolyl |

Examples 1-5

As is stated above, these Examples were prepared in analogy with previously published procedures in *J. Org. Chem.* 2001, 66(20), 6756-6761.

Example 6

By following the general procedure for nitration, 751 mg (1.77 mmol) Example 1 was converted to 536 mg Example 6 (64%). $[\alpha]_D$ −206 (c 0.5, CHCl$_3$); $^1$H NMR (400 MHz, CDCl$_3$) 7.72-7.67 (m, 1H), 7.64-7.45 (m, 3H), 5.79-5.73 (m, 1H), 3.83 (s (splitted), 3H), 3.82-3.75 (dd, J=11.9, 8.8 Hz, 1H), 3.54-3.48 (m, 1H), 2.36-2.15 (m, 2H), 1.31-1.09 (m, 3H), 0.59-0.51 (m, 6H); $^{13}$C NMR (100 MHz, CDCl$_3$) 167.6 (splitted), 153.5 (splitted), 151.7 (splitted), 148.7 (splitted), 138.4 (splitted), 135.7 (splitted), 134.0 (splitted), 131.6 (q (splitted), J=32.4 Hz), 129.9 (splitted), 127.5-127.1 (m), 125.9 (m), 123.8 (q, J=272.5 Hz), 112.7, 64.4 (splitted), 53.7 (splitted), 38.0 (splitted), 32.1 (splitted), 28.1, 27.7, 21.3, 21.5 (splitted).

Example 7

By following the general procedure for nitration, 731 mg (1.78 mmol) Example 2 was converted to 586 mg (72%) Example 7. $[\alpha]_D$ −215 (c 0.5, CHCl$_3$); $^1$H NMR (400 MHz, CDCl$_3$) 7.70 (d, 1H), 7.64-7.45 (m, 3H), 5.78-5.73 (m, 1H), 3.83 (s (splitted), 3H), 3.78 (dd, J=11.9, 8.8 Hz, 1H), 3.55-3.48 (m, 1H), 2.36-2.18 (m, 2H), 1.39-1.18 (m, 2H), 1.12-0.99 (m, 2H), 0.59 (t (splitted), J=7.4 Hz, 3H); $^{13}$C NMR (100 MHz, CDCl$_3$) 167.7 (splitted), 153.6, 151.8, 148.6, 138.5, 135.9 (splitted), 134.1, 133.9, 131.7 (q (splitted), J=32.6 Hz), 130.0 (splitted), 127.6-127.1 (m), 126.1 (m), 123.8 (q, J=272.4 Hz), 112.8, 64.5 (splitted), 53.8 (splitted), 32.2 (splitted), 31.2 (splitted), 29.4, 22.7, 13.2 (splitted).

Example 8

By following the general procedure for nitration, 776 mg (1.77 mmol) Example 3 was converted to 557 mg (65%) Example 8. $[\alpha]_D$ −203 (c 0.5, CHCl$_3$); $^1$H NMR (400 MHz, CDCl$_3$) 7.72-7.68 (m, 1H), 7.64-7.45 (m, 3H), 5.78-5.74 (m, 1H), 3.83 (s (splitted), 3H), 3.78 (dd, J=8.8, 11.9 Hz, 1H), 3.54-3.48 (m, 1H), 2.36-2.16 (m, 2H), 1.39-1.20 (m, 2H), 1.10-0.98 (m, 4H), 0.98-0.88 (m, 2H), 0.72 (t, J=7.1 Hz, 3H); $^{13}$C NMR (100 MHz, CDCl$_3$) 167.6 (splitted), 153.6, 151.8 (splitted), 148.5, 138.4 (splitted), 135.8 (splitted), 133.9 (d, J=25.0 Hz), 131.6 (dq, J=32.5, 8.5 Hz), 129.9 (splitted), 127.3 (dq, J=26.1, 3.5 Hz), 126.0 (broad, splitted), 123.7 (q, J=272.5 Hz), 112.7, 64.4 (splitted), 53.7 (splitted), 32.1 (broad), 30.7, 29.6 (broad), 29.1, 29.0, 22.1, 13.8.

Example 9

By following the general procedure for nitration, 2062 mg (5.58 mmol) Example 4 was converted to 1320 mg Example 9 (57%). $[\alpha]_D$ −223 (c 0.5, CHCl$_3$); $^1$H NMR (400 MHz, CDCl$_3$) 7.72-7.65 (m, 1H), 7.65-7.42 (m, 3H), 5.75 (dd, J=8.8, 2.0 Hz, 1H), 3.82 (s, 3H), 3.80-3.74 (m, 1H), 3.56-3.49 (m, 1H), 1.98 (s, 3H); $^{13}$C NMR (100 MHz, CDCl$_3$) 167.5, 153.3, 151.6, 144.7, 138.7, 135.9 (splitted), 133.7 (splitted), 131.7 (q, J=32.6 Hz), 130.0, 127.0 (m), 126.0 (splitted), 123.8 (q, J=272.7 Hz), 113.1, 64.7 (splitted), 53.7 (splitted), 32.1, 16.7.

Example 10

By following the general procedure for nitration, 1178 mg (2.60 mmol) Example 5 was converted to 796 mg (61%) Example 10. $^1$H NMR (400 MHz, CDCl$_3$) 7.67-7.61 (m, 1H), 7.60-7.40 (m, 3H), 5.76-5.71 (m, 1H), 3.81-3.71 (m, 1H), 3.75 (s, 3H), 3.45 (d, J=11.7 Hz, 1H), 2.29-2.10 (m, 2H), 1.34-1.13 (m, 2H), 1.11-1.00 (m, 2H), 1.00-0.83 (m, 6H), 0.69 (t, J=7.1 Hz, 3H); $^{13}$C NMR (100 MHz, CDCl$_3$) 167.5 (splitted), 153.3 (splitted), 152.1 (broad), 148.2, 138.0, 135.7 (splitted), 133.8 (d, J=14.5 Hz), 131.2 (q (splitted), J=32.6 Hz), 129.7 (splitted), 127.0 (m), 125.6 (m), 123.5 (q, J=272.7 Hz), 112.4, 64.3 (splitted), 53.3 (splitted), 31.9 (splitted), 31.0, 29.3, 29.1, 28.8, 27.9, 22.2, 13.6.

Example 11

By following the general procedure for reduction, 408 mg (0.867 mmol) Example 6 was converted to 323 mg (86%) Example 11. $[\alpha]_D$ −105 (c 0.5, CHCl$_3$); $^1$H NMR (400 MHz, CDCl$_3$) 7.58 (d, J=7.8 Hz, 1H), 7.53-7.45 (m, 2H), 7.43-7.38 (m, 1H), 5.61 (d, J=7.9 Hz, 1H), 4.05 (bs, 2H), 3.77 (s, 3H), 3.64-3.56 (m, 1H), 3.42-3.36 (m, 1H), 2.17-2.05 (m, 2H), 1.37-1.25 (m, 1H), 1.25-1.12 (m, 2H), 0.64 (d, J=6.3 Hz, 6H); $^{13}$C NMR (100 MHz, CDCl$_3$) 168.5, 156.7, 138.3, 133.8, 133.4, 131.2 (d, J=12.3 Hz), 130.9 (q (splitted), J=32.5), 129.1 (splitted), 128.3 (broad), 124.7 (m), 123.8 (q (splitted), J=272.3), 115.4 (splitted), 63.8 (splitted), 53.2 (splitted), 36.0, 31.9 (splitted), 28.2, 26.3 (splitted), 21.9 (2C).

Example 12

By following the general procedure for reduction, 429 mg (0.940 mmol) Example 7 was converted to 359 mg (90%) Example 12. $[\alpha]_D$ −112 (c 0.5, CHCl$_3$); $^1$H NMR (400 MHz, CDCl$_3$) 7.57 (d, J=7.8 Hz, 1H), 7.51-7.43 (m, 2H), 7.42-7.36 (m, 1H), 5.60 (dd, J=8.3, 2.0 Hz, 1H), 4.00 (bs, 2H), 3.75 (s, 3H), 3.63-3.54 (m, 1H), 3.41-3.34 (m, 1H), 2.13 (t, J=8.2 Hz, 2H), 1.37-1.20 (m, 2H), 1.16-1.04 (m, 2H), 0.65 (t, J=7.3 Hz, 3H); $^{13}$C NMR (100 MHz, CDCl$_3$) 167.3, 155.5, 137.2 (splitted), 132.5, 132.2, 130.2, 129.9, 129.6 (q (splitted), J=32.5 Hz), 127.9 (splitted), 126.0-125.4 (m), 123.4 (m), 122.7 (q (splitted), J=272.4 Hz), 114.2, 62.6, 52.0, 30.7, 28.0, 26.8, 21.4.

Example 13

By following the general procedure for reduction, 405 mg (0.836 mmol) Example 8 was converted to 351 mg (92%) Example 13. $[\alpha]_D$ −107 (c 0.5, CHCl$_3$); $^1$H NMR (400 MHz, CDCl$_3$) 7.56-7.51 (m, 1H), 7.48-7.40 (m, 2H), 7.39-7.32 (m, 1H), 5.57 (d, J=7.7 Hz, 1H), 4.04 (bs, 2H), 3.71 (s, 3H), 3.59-3.51 (m, 1H), 3.36-3.30 (m, 1H), 2.14-2.05 (m, 2H), 1.35-1.19 (m, 2H), 1.11-0.92 (m, 6H), 0.72-0.64 (t, J=7.0 Hz, 3H); $^{13}$C NMR (100 MHz, CDCl$_3$) 168.4, 156.5, 138.3 (splitted), 133.5 (d, J=33.8 Hz), 131.3, 130.8, 130.7 (dq, J=31.9, 8.8 Hz), 128.9 (splitted), 127.8, 126.9 (broad, splitted), 124.4 (broad, splitted), 123.8 (dq, J=272.2, 3.2 Hz), 115.2, 63.7 (splitted), 52.9 (splitted), 31.7 (broad), 30.9, 29.0, 28.1, 26.8, 22.1, 13.6.

Example 14

By following the general procedure for reduction, 1165 mg (2.81 mmol) Example 9 was converted to 891 mg (82%) Example 14. $[\alpha]_D$ −125 (c 0.5, CHCl$_3$); $^1$H NMR (400 MHz, CDCl$_3$) 7.61 (d, J=7.8 Hz, 1H), 7.56-7.49 (m, 2H), 7.42 (d, J=7.4 Hz, 1H), 5.67 (dd, J=8.2, 2.2 Hz, 1H), 3.98 (bs, 2H), 3.82 (s, 3H), 3.63 (dd, J=11.6, 2.2 Hz, 1H), 3.45 (dd, J=11.6, 8.2 Hz, 1H), 1.84 (s, 3H); $^{13}$C NMR (100 MHz, CDCl$_3$) 167.7 (splitted), 153.6, 151.8, 148.6, 138.5, 135.9 (splitted), 134.1, 133.9, 131.7 (q (splitted), J=32.6 Hz), 130.0 (splitted), 127.6-127.1 (m), 126.1 (m), 123.8 (q, J=272.4 Hz), 112.8, 64.5 (splitted), 53.8 (splitted), 32.2 (splitted), 31.2 (splitted), 29.4, 22.7, 13.2 (splitted).

Example 15

By following the general procedure for reduction, 758 mg (1.52 mmol) Example 10 was converted to 634 mg (89%) Example 15. $^1$H NMR (400 MHz, CDCl$_3$) 7.54-7.49 (m, 1H), 7.47-7.30 (m, 3H), 5.55 (d, J=7.8 Hz, 1H), 4.05 (bs, 2H), 3.68 (s, 3H), 3.58-3.49 (m, 1H), 3.31 (d, J=11.6 Hz, 1H), 2.13-2.03 (m, 2H), 1.33-1.17 (m, 2H), 1.12-0.93 (m, 8H), 0.69 (t, J=7.0 Hz, 3H); $^{13}$C NMR (100 MHz, CDCl$_3$) 168.3, 156.4, 138.2 (splitted), 133.4 (d, J=32.2 Hz), 131.3, 130.7, 130.6 (q (splitted), J=32.3 Hz), 128.9 (splitted), 127.6, 126.7 (m), 124.3, 123.6 (q (splitted), J=272.6 Hz), 115.12, 63.6 (splitted), 52.8 (splitted), 31.6, 31.2, 29.2, 28.3, 28.1, 26, 22.2, 13.6.

Example 16

By following the general procedure for pyrazole formation, 200 mg (0.454 mmol) Example 11 was converted to 180 mg (88%) Example 16. [α]$_D$ –145 (c 0.5, CHCl$_3$); $^1$H NMR (400 MHz, CDCl$_3$) 12.87 (bs, 1H), 7.71-7.62 (m, 2H), 7.62-7.53 (m, 2H), 5.86 (d, J=7.8 Hz, 1H), 3.81 (s, 3H), 3.73 (dd, J=11.7, 7.8 Hz, 1H), 3.56 (d, J=11.7 Hz, 1H), 2.28-2.16 (m, 2H), 1.37-1.23 (m, 1H), 0.63-0.47 (m, 6H); $^{13}$C NMR (100 MHz, CDCl$_3$) 168.5, 153.5, 145.0, 136.9, 135.3, 133.5 (splitted), 132.0 (broad), 131.0 (q (splitted), J=32.5 Hz), 129.2 (splitted), 127.3-126.8 (m), 125.0 (m), 123.9 (m), 124.0 (q, J=272.1 Hz), 108.6 (splitted), 62.5, 53.4, 36.2, 32.6, 29.0 (splitted), 22.1 (splitted), 21.9 (splitted).

Example 17

By following the general procedure for pyrazole formation, 249 mg (0.584 mmol) Example 12 was converted to 218 mg (85%) Example 17. [α]$_D$ –163 (c 0.5, CHCl$_3$); $^1$H NMR (400 MHz, CDCl$_3$) 13.04 (bs, 1H), 7.69-7.63 (m, 2H), 7.61-7.53 (m, 2H), 5.85 (d, J=7.6 Hz, 1H), 3.80 (s, 3H), 3.72 (dd, J=11.6, 7.6 Hz, 1H), 3.55 (d, br, J=11.6 Hz, 1H), 2.36-2.19 (m, 2H), 1.33-1.17 (m, 2H), 0.58 (t, J=7.3 Hz, 3H); $^{13}$C NMR (100 MHz, CDCl$_3$) 168.5, 153.5, 145.6, 136.9, 135.3, 133.3 (splitted), 132.0 (broad), 131.0 (q (splitted), 32.3 Hz), 129.2 (splitted), 126.8 (m), 125.0 (m), 124.0 (q, J=272.6 Hz), 123.7 (m), 108.5 (splitted), 62.5 (splitted), 53.4, 32.6, 29.3 (splitted), 22.9, 13.6.

Example 18

By following the general procedure for pyrazole formation, 209 mg (0.460 mmol) Example 13 was converted to 159 mg (74%) Example 18. [α]$_D$ –154 (c 0.5, CHCl$_3$); $^1$H NMR (400 MHz, CDCl$_3$) 12.27 (bs, 1H), 7.71-7.64 (m, 2H), 7.62-7.54 (m, 2H), 5.86 (d, J=7.7 Hz, 1H), 3.82 (s, 3H), 3.73 (dd, J=11.6, 7.7 Hz, 1H), 3.56 (d, J=11.6 Hz, 1H), 2.41-2.22 (m, 2H), 1.30-1.12 (m, 2H), 1.09-0.97 (m, 2H), 0.97-0.85 (m, 2H), 0.75-0.66 (t, J=7.2 Hz, 3H); $^{13}$C NMR (100 MHz, CDCl$_3$) 168.5, 153.5, 146.1, 137.0 (splitted), 135.3, 133.3 (splitted), 131.9 (broad), 131.1 (q (splitted), J=32.5 Hz), 129.2 (splitted), 126.8 (m), 125.1 (m), 124.0 (q, J=272.5 Hz), 123.7, 108.6 (splitted), 62.5, 53.5 (splitted), 32.7, 31.5, 29.4 (splitted), 27.6, 22.2, 13.8.

Example 19

By following the general procedure for pyrazole formation, 297 mg (0.773 mmol) Example 14 was converted to 83 mg (27%) Example 19. [α]$_D$ –237 (c 0.5, CHCl$_3$); $^1$H NMR (400 MHz, CDCl$_3$) 13.27 (bs, 1H), 7.83-7.75 (m, 2H), 7.71 (d, J=7.3 Hz, 1H), 7.67-7.56 (m, 2H), 5.90 (d, J=7.6 Hz, 1H), 3.83 (s, 3H), 3.78 (dd, J=11.7, 7.6 Hz, 1H), 3.66-3.61 (m, 1H); $^{13}$C NMR (100 MHz, CDCl$_3$) 168.5, 153.3, 136.9, 135.6, 132.2 (broad), 132.0, 131.4 (q, J=32.5 Hz), 131.2 (broad), 129.6, 127.1 (broad), 125.5 (m), 124.8 (m), 124.0 (q, J=272.5 Hz), 108.1, 62.4, 53.6, 32.3.

Example 20

By following the general procedure for pyrazole formation, 470 mg (1.00 mmol) Example 15 was converted to 388 mg (81%) Example 20. $^1$H NMR (400 MHz, CDCl$_3$) 13.60 (bs, 1H), 7.68-7.62 (m, 2H), 7.60-7.52 (m, 2H), 5.84 (d, J=7.6 Hz, 1H), 3.78 (s, 3H), 3.76-3.68 (m, 1H), 3.53 (d, J=11.5 Hz, 1H), 2.39-2.22 (m, 2H), 1.25-1.12 (m, 2H), 1.12-1.20 (m, 2H), 1.00-0.87 (m, 4H), 0.74 (t, J=7.2 Hz, 3H); $^{13}$C NMR (100 MHz, CDCl$_3$) 168.6, 153.5, 146.3 (broad), 137.1 (splitted), 135.3 (splitted), 133.4 (splitted), 131.8 (broad), 131.0 (q (splitted), J=32.6 Hz), 129.2 (splitted), 126.9 (m), 125.1 (m), 123.7 (broad), 124.0 (q, J=272.5 Hz), 108.6 (splitted), 62.6 (splitted), 53.4, 32.7, 31.4, 29.8 (splitted), 29.1, 27.7 (broad), 22.5, 14.0.

Example 21

(7R)-3-isobutyl-9-oxo-4-[3-(trifluoromethyl)phenyl]-1,6,7,9-tetrahydropyrazolo[4,3-d][1,3]thiazolo[3,2-a]pyridine-7-carboxylic acid By following the general procedure for hydrolysis using in total 1.6 equiv. of LiOH, 63 mg (0.140 mmol) Example 16 was converted to 61 mg (quant.) Example 21. [α]$_D$ –110 (c 0.5, MeOH); $^1$H NMR (400 MHz, MeOD-d$_4$) 7.78-7.73 (m, 1H), 7.73-7.62 (m, 3H), 5.74 (d, J=8.1 Hz, 1H), 3.86 (dd, J=11.7, 8.1 Hz, 1H), 3.60 (d, J=11.7 Hz, 1H), 2.25-2.19 (m, 2H), 1.30-1.18 (m, 1H), 0.59-0.49 (m, 6H); $^{13}$C NMR (100 MHz, MeOD-d$_4$) 171.3 (splitted), 156.1, 143.0, 138.7, 137.5, 136.3, 135.2 (splitted), 132.1 (dq, J=32.4, 7.2=Hz), 130.8 (splitted), 128.1 (m), 126.0 (m), 125.4 (q, J=271.6 Hz), 123.9 (splitted), 108.8, 63.6, 36.3 (splitted), 33.3, 30.3 (splitted), 22.4 (splitted), 22.2 (splitted).

Example 22

(7R)-9-oxo-3-propyl-4-[3-(trifluoromethyl)phenyl]-1,6,7,9-tetrahydropyrazolo[4,3-d][1,3]thiazolo[3,2-a]pyridine-7-carboxylic acid By following the general procedure for hydrolysis using in total 1.6 equiv. of LiOH, 61 mg (0.139 mmol) Example 17 was converted to 59 mg (quant.) Example 22. [α]$_D$ –119 (c 0.5, MeOH); $^1$H NMR (400 MHz, MeOD-d$_4$) 7.78-7.62 (m, 4H), 5.77-5.72 (m, 1H), 3.86 (dd, J=11.8, 8.2 Hz, 1H), 3.60 (d, J=11.8 Hz, 1H), 2.34-2.19 (m, 2H), 1.26-1.15 (m, 2H), 0.58 (t, J=7.3 Hz, 3H); $^{13}$C NMR (100 MHz, MeOD-d$_4$) 171.3, 156.0, 143.9, 138.7, 137.4, 135.9, 135.0, 132.0, 130.7, 127.9, 126.1, 125.4, 123.8, 108.8, 63.8, 33.3, 29.4, 24.1, 13.9.

Example 23

(7R)-9-oxo-3-pentyl-4-[3-(trifluoromethyl)phenyl]-1,6,7,9-tetrahydropyrazolo[4,3-d][1,3]thiazolo[3,2-a]pyridine-7-carboxylic acid By following the general procedure for hydrolysis using in total 1.7 equiv. of LiOH, 65 mg (0.140 mmol) Example 18 was converted to 63 mg (quant.) Example 23. $[\alpha]_D$ −113 (c 0.5, MeOH); $^1$H NMR (400 MHz, MeOD-$d_4$) 7.77-7.63 (m, 4H), 5.74.5-71 (m, 1H), 3.86 (dd, J=11.7, 8.2 Hz, 1H), 3.59 (d, J=11.7 Hz, 1H), 2.39-2.23 (m, 2H), 1.21-1.10 (m, 2H), 1.10-0.98 (m, 2H), 0.97-0.84 (m, 2H), 0.73 (t, J=7.3 Hz, 3H); $^{13}$C NMR (100 MHz, MeOD-$d_4$) 171.3 (splitted), 156.0, 144.1, 138.8, 137.5, 135.9, 135.1 (splitted), 132.1 (q (splitted), J=32.6 Hz), 130.7 (splitted), 127.9 (m), 127.1 (m), 125.4 (q, J=271.7 Hz), 123.8, 108.8, 68.8, 63.8, 33.3, 32.6, 30.7, 27.6, 23.1.

Example 24

(7R)-9-oxo-4-[3-(trifluoromethyl)phenyl]-1,6,7,9-tetrahydropyrazolo[4,3-d][1,3]thiazolo[3,2-a]pyridine-7-carboxylic acid By following the general procedure for hydrolysis using in total 1.8 equiv. of LiOH, 55 mg (0.139 mmol) Example 19 was converted to 53 mg (quant.) Example 24. $[\alpha]_D$ −214 (c 0.5, DMSO); $^1$H NMR (400 MHz, DMSO-$d_6$) 14.25 (bs, 1H), 7.86-7.72 (m, 5H), 5.64 (d, J=8.2 Hz, 1H), 3.87 (dd, J=11.7, 8.2 Hz, 1H), 3.62 (d, J=11.7 Hz, 1H).

Example 25

(7R)-3-hexyl-9-oxo-4-[3-(trifluoromethyl)phenyl]-1,6,7,9-tetrahydropyrazolo[4,3-d][1,3]thiazolo[3,2-a]pyridine-7-carboxylic acid By following the general procedure for hydrolysis using in total 2.0 equiv. of LiOH, 336 mg (0.701 mmol) Example 20 was converted to 251 mg (77%) Example 25 after purification with silica gel chromatography using $CH_2Cl_2$:MeOH:AcOH (100:1:1→100:2:1) as eluent. $[\alpha]_D$ −117 (c 0.5, MeOH); $^1$H NMR (400 MHz, MeOD-$d_4$) 7.74-7.60 (m, 4H), 5.74 (d, J=8.0 Hz, 1H), 3.84 (dd, J=11.6, 8.0 Hz, 1H), 3.57 (d, J=11.6 Hz, 1H), 2.39-2.21 (m, 2H), 1.19-1.04 (m, 4H), 1.01-0.86 (m, 4H), 0.77 (t, J=7.3 Hz, 3H); $^{13}$C NMR (100 MHz, MeOD-$d_4$) 171.3 (splitted), 155.8, 144.2, 138.6, 137.4, 135.7 (splitted), 134.8 (splitted), 132.0 (q (splitted), J=32.3 Hz), 130.7 (splitted), 127.8 (m), 126.0 (m), 125.2 (q (splitted), J=272.1 Hz), 123.7 (splitted), 108.7, 63.8, 33.3, 32.3, 30.9, 30.0, 27.7, 23.4, 14.3.

Example 26

82 mg $PPh_3$ was dissolved in 0.15 ml THF and 0.15 ml $CH_2Cl_2$ and cooled to 0° C. 27 µl DEAD was added and the solution was stirred for one hour. This was then transferred to a solution of 55 mg (0.122 mmol) Example 16 and 9 µl ethanol in 0.15 ml THF and 0.15 ml $CH_2Cl_2$ at rt. The solution was then stirred 4 h before concentration under reduced pressure. The crude product was passed through a silica gel column using heptane:ethyl acetate 2:1→1:1 as eluent. To remove DEAD-$H_2$ the product was dissolved in diethyl ether and washed five times with 10% NaOH (aq.). The combined aqueous phases were extracted once with diethyl ether and the combined organic phases were passed through a silica plug and concentrated under reduced pressure to 23 mg (39%) of Example 26. $[\alpha]_D$ −102 (c 0.5, $CHCl_3$); $^1$H NMR (400 MHz, $CDCl_3$) 7.71-7.54 (m, 4H), 5.72-5.66 (m, 1H), 4.82-4.61 (m, 2H), 3.58 (s, 3H), 3.71 (dd, br, J=11.7, 8.0 Hz, 1H), 3.56-3.49 (m, 1H), 2.16-2.08 (m, 2H), 1.52-1.42 (t, J=7.2 Hz, 3H), 1.33-1.21 (m, 1H), 0.61-0.48 (m, 6H).

Example 27

(7R)-1-ethyl-3-isobutyl-9-oxo-4-[3-(trifluoromethyl)phenyl]-1,6,7,9-tetrahydropyrazolo[4,3-d][1,3]thiazolo[3,2-a]pyridine-7-carboxylic acid By following the general procedure for hydrolysis using in total 1.0 equiv. of LiOH and additional 0.25 ml THF, 15 mg (0.031 mmol) Example 26 was converted to 14 mg (quant.) Example 27. $[\alpha]_D$ −84 (c 0.5, MeOH); $^1$H NMR (400 MHz, MeOD-$d_4$) 7.79-7.72 (m, 1H), 7.72-7.62 (m, 3H), 5.63 (d, J=7.6 Hz, 1H), 4.75-4.62 (m, 2H), 3.86-3.77 (m, 1H), 3.60 (d, J=11.4 Hz, 1H), 2.19-2.09 (m, 2H), 1.91-1.82 (m, 1H), 1.48-1.38 (m, 3H), 1.35-1.17 (m, 3H), 0.60-0.45 (m, 6H).

Example 28

(7R)-4-(3,4-difluorophenyl)-3-hexyl-9-oxo-1,6,7,9-tetrahydropyrazolo[4,3-d][1,3]thiazolo[3,2-a]pyridine-7-carboxylic acid Example 28 was synthesized in analogy with Example 25, except from the pyrazole forming step which was conducted as follows: 72 mg (0.165 mmol) VI ($R^1$=3,4-difluorophenyl, $R^2$=1-hexyl) and 12.5 mg $NaNO_2$ (0.18 mmol) was dissolved in 1.5 ml methanol and 0.5 ml acetic acid and allowed to stir at rt for 1 h. The solvent was removed under reduced pressure and the crude product was purified with silica gel chromatography using heptane:ethyl acetate (1:1) as eluent to yield 39 mg (53%) VII ($R^1$=3,4-difluorophenyl, $R^2$=1-hexyl). After hydrolysis according to general procedure (VIII) using in total 1.7 equiv. of LiOH, Example 28 was obtained. $^1$H NMR (400 MHz, MeOH-$d_4$) 7.49-7.30 (m, 2H), 7.30-7.15 (m, 1H), 5.72 (d, J=8.0 Hz, 1H), 3.84 (dd, J=11.7, 8.0 Hz, 1H), 3.60 (d, J=11.7 Hz, 1H), 2.49-2.28 (m, 2H), 1.31-1.12 (m, 4H), 1.12-0.97 (m, 4H), 0.84 (t, J=7.3 Hz, 3H).

Example 29

(7R)-4-(3,4-difluorophenyl)-3-hexyl-9-oxo-N-(phenylsulfonyl)-1,6,7,9-tetrahydropyrazolo[4,3-d][1,3]thiazolo[3,2-a]pyridine-7-carboxamide 34 mg (0.21 mmol) N,N'-carbonyldiimidazole was added to a solution of 30 mg (0.069 mmol) Example 28 dissolved in 1.5 ml $CH_2Cl_2$ at rt. After one hour of stirring, 44 mg (0.28 mmol) benzenesulfonamide was added and the mixture was stirred in a sealed tube at 80° C. for 7 h using microwave heating. The mixture was diluted with $CH_2Cl_2$ and washed with 5% aqueous acetic acid, extracted with $CH_2Cl_2$ and then concentrated. The crude product was purified with silica gel chromatography using ethyl acetate:methanol (9:1) as eluent, yielding 16 mg (40%) Example 29. $^1$H NMR (400 MHz, DMSO-$d_6$, 323 K) 13.53 (bs, 1H), 7.79-7.31 (m, 8H), 5.32 (d, J=8.2 Hz, 1H), 7.70 (dd, J=11.1, 8.2 Hz, 1H), 3.53 (d, J=11.1 Hz, 1H), 2.32-2.20 (m, 2H), 1.24-1.06 (m, 4H), 1.06-0.91 (m, 4H), 0.79 (t, J=7.2 Hz, 3H).

Example 32

(3R)-6-amino-2,3-dihydro-7-methyl-8-phenyl-thiazolo[3,2-a]pyridine-5-one-3-carboxylic acid methyl ester Example 32 was prepared by first following the general procedure for nitration, but then directly reduced following the general procedure for reduction without column purification between the two steps. Starting from 3.01 g (9.99 mmol) of Example 30, 2.26 g (71%) of Example 32 was obtained as white foam. [α]$_D$ −169 (c 0.5, CHCl$_3$); IR λ 1745, 1637, 1577, 1311, 1209, 1176, 707 cm$^{-1}$; $^1$H NMR (400 MHz, CDCl$_3$) δ 7.43-7.30 (m, 3H), 7.24-7.17 (m, 2H), 5.67-5.62 (m, 1H), 3.89 (bs, 2H), 3.82-3.78 (m, 3H), 3.63-3.55 (m, 1H), 3.44-3.48 (m, 1H), 1.85-1.83 (m, 3H); $^{13}$C NMR (100 MHz, CDCl$_3$) δ 168.8, 156.4, 137.6, 131.7, 130.9, 130.1, 129.8, 128.7, 128.6, 127.9, 124.6, 117.3, 63.8, 53.3, 32.0, 14.9;); HRMS (FAB$^+$) calcd [M+H]$^+$ C$_{16}$H$_{17}$N$_2$O$_3$S$^+$ 317.0954, obsd 317.0961

Example 33

(3R)-6-amino-2,3-dihydro-7-(3-methyl-butyl)-8-phenyl-thiazolo[3,2-a]pyridine-5-one-3-carboxylic acid methyl ester Example 33 was prepared by first following the general procedure for nitration, but then directly reduced following the general procedure for reduction without column purification between the two steps. Starting from 158 mg (0.442 mmol) of Example 31, 110 mg (67%) of Example 33 was obtained as slightly gray foam. [α]$_D$ −149 (c 0.5, CHCl$_3$); IR λ 1745, 1635, 1571, 1309, 1207, 1168, 701 cm$^{-1}$; $^1$H NMR (400 MHz, CDCl$_3$) δ 7.41-7.30 (m, 3H), 7.24-7.18 (m, 2H), 5.61 (dd, J=8.3, 2.3 Hz, 1H), 3.91 (bs, 2H), 3.80 (s, 3H), 3.58 (dd, J=11.7, 8.3 Hz, 1H), 3.39 (dd, J=11.7, 2.3 Hz, 1H), 2.19 (dd, J=9.7, 7.1 Hz, 2H), 1.41-1.29 (m, 1H), 1.28-1.16 (m, 2H), 0.68 (d, J=6.5 Hz, 6H); $^{13}$C NMR (100 MHz, CDCl$_3$) δ 168.7, 156.8, 137.5, 131.1, 131.0, 130.3, 129.8, 129.5, 128.6, 128.5, 128.0, 117.0, 63.9, 53.2, 36.1, 31.9, 28.3, 26.4, 22.1 (2C); HRMS (FAB$^+$) calcd [M+H]$^+$ C$_{20}$H$_{25}$N$_2$O$_3$S$^+$ 373.1580, obsd 373.1587.

Example 34

(7R)-6,7-dihydro-4-phenyl-pyrazolo[4,5-d]thiazolo[3,2-a]pyridine-9-one-7-carboxylic acid methyl ester Example 34 was prepared according to the general procedure for pyrazole formation, but excluding methanol as additive in the column purification. Scavenging of unreacted starting material using amberlite was not needed. 598 mg of Example 32 (1.89 mmol) was converted to 190 mg (31%) of Example 34. [α]$_D$ (c 0.5, CHCl$_3$); IR λ 1743, 1654, 1211, 1180, 698 cm$^{-1}$; $^1$H NMR (400 MHz, CDCl$_3$) δ 7.83-7.79 (s, 1H), 7.55-7.43 (m, 4H), 7.42-7.35 (m, 1H), 5.87 (dd, J=7.7, 1.3 Hz, 1H), 3.83 (s, 3H), 3.72 (dd, J=11.6, 7.7 Hz, 1H), 3.60 (dd, J=11.6, 1.3 Hz, 1H); $^{13}$C NMR (100 MHz, CDCl$_3$) δ 168.6, 153.3, 136.0, 134.6, 132.9 (broad), 130.9 (broad), 128.9 (2C), 128.6 (2C), 128.1, 127.6, 109.7, 62.3, 53.5, 32.6; HRMS (FAB$^+$) calcd [M+H]$^+$ C$_{16}$H$_{14}$N$_3$O$_3$S$^+$ 328.0750, obsd 328.0757.

Example 35

(7R)-6,7-dihydro-3-isobutyl-4-phenyl-pyrazolo[4,5-d]thiazolo[3,2-a]pyridine-9-one-7-carboxylic acid methyl ester Example 35 was prepared according to the general procedure for pyrazole formation, but excluding methanol as additive in the column purification. Scavenging of unreacted starting material using amberlite was not needed. 150 mg of Example 33 (0.403 mmol) was converted to 84 mg (54%) of D. [α]$_D$ −224 (c 0.5, CHCl$_3$); IR λ 1747, 1654, 1565, 1205, 1170, 700 cm$^{-1}$; $^1$H NMR (400 MHz, CDCl$_3$) δ 7.48-7.40 (m, 3H), 7.40-7.33 (m, 2H), 5.84 (dd, J=7.8, 1.5 Hz, 1H), 3.83 (s, 3H), 3.70 (dd, J=11.6, 7.8 Hz, 1H), 3.54 (dd, J=11.6, 1.5 Hz, 1H), 2.31-2.21 (m, 2H), 1.42-1.31 (m, 1H), 0.59 (d, J=6.6 Hz, 3H), 0.55 (d, J=6.6 Hz, 3H); $^{13}$C NMR (100 MHz, CDCl$_3$) δ 168.8, 153.5, 145.9 (broad), 136.1, 134.7, 131.8 (broad), 130.2, 129.9, 128.7, 128.6, 128.4, 124.5, 110.3, 62.5, 53.5, 36.3, 32.7, 29.0, 22.3, 22.1; HRMS (FAB$^+$) calcd [M+H]$^+$ C$_{20}$H$_{22}$N$_3$O$_3$S$^+$ 384.1376, obsd 384.1378.

Bromination of Example 34

Example 36

(7R)-3-bromo-6,7-dihydro-4-phenyl-pyrazolo[4,5-d]thiazolo[3,2-a]pyridine-9-one-7-carboxylic acid methyl ester 9.2 ml THF was added to a mixture of 602 mg (1.84 mmol) of Example 34 and 199 mg (2.03 mmol) KOAc. When Example 34 had been dissolved, 99 μl (1.93 mmol) Br$_2$ was added drop-wise while stirring at rt. The mixture was stirred for 1 h and the reaction was then quenched by addition of 10% Na$_2$S$_2$O$_5$ (aq.). Ethyl acetate was added and the organic phase was separated. The aqueous phase was extracted with ethyl acetate and the combined organic phases were dried over Na$_2$SO$_4$(s), filtrated and concentrated under reduced pressure. The residue was dissolved in a small amount of THF (occasionally the product had to be concentrated from a larger volume of THF to avoid precipitation during column chromatography) and then purified with silica gel chromatography using heptane:ethyl acetate (2:1→1:2) as eluent. 622 mg (83%) of Example 36 was afforded as pale yellow foam. [α]$_D$ −183 (c 0.5, DMSO); IR λ 1745, 1652, 1562, 1149, 698 cm$^{-1}$; $^1$H NMR (400 MHz, DMSO-d$_6$) δ 14.60 (bs, 1H), 7.49-7.40 (m, 3H), 7.40-7.27 (m, 2H), 5.79-5.75 (m, 1H), 3.85 (dd, J=11.9, 8.5 Hz, 1H), 3.76 (s, 3H), 3.57 (dd, J=11.9, 1.2 Hz, 1H); $^{13}$C NMR (100 MHz, DMSO-d$_6$) δ 168.7, 151.2, 137.7, 133.7, 131.2, 130.6 (broad), 130.1 (broad), 128.3 (2C), 128.2, 123.7, 118.5, 106.2, 62.1, 53.1, 31.7; HRMS (FAB$^+$) calcd [M+H]$^+$ C$_{16}$H$_{13}$BrN$_3$O$_3$S$^+$ 405.9855, obsd 405.9857

Example 37

(7R)-6,7-dihydro-3-isobutyl-4-phenyl-pyrazolo[4,5-d]thiazolo[3,2-a]pyridine-9-one-7-carboxylic acid By following the general procedure for hydrolysis, using in total 1.5 ml 0.1 M LiOH (aq.), 38 mg (0.10 mmol) of Example 35 was converted to 36 mg (97%) of Example 37. [α]$_D$ −179 (c 0.25, HCO$_2$H); IR λ 1648, 1565, 1365, 1166, 700 cm$^{-1}$; $^1$H NMR (400 MHz, MeOH-d$_4$) δ 7.49-7.40 (m, 3H), 7.40-7.32 (m, 2H), 5.64 (d, J=7.9 Hz, 1H), 3.75 (dd, J=11.5, 7.9 Hz, 1H), 3.55 (d, J=11.5 Hz, 1H), 2.32-2.17 (m, 2H), 1.33-1.21 (m, 1H), 0.54 (d, J=6.6 Hz, 3H), 0.51 (d, J=6.6 Hz, 3H); $^{13}$C NMR (100 MHz, MeOH-d$_4$) δ 172.6, 156.0, 143.6 (broad), 137.8, 137.1, 136.0 (broad), 131.4, 131.2, 129.7, 129.5, 129.2, 124.5 (broad), 110.3, 64.9, 36.4, 33.6, 30.2, 22.6, 22.2; HRMS (FAB$^+$) calcd [M+H]$^+$ C$_{19}$H$_{20}$N$_3$O$_3$S$^+$ 370.1220, obsd 370.1229

Example 38

(7R)-6,7-dihydro-3,4-diphenyl-pyrazolo[4,5-d]thiazolo[3,2-a]pyridine-9-one-7-carboxylate By following the general procedure for Suzuki coupling of Example 36 using 44 mg (0.36 mmol) phenylboronic acid as coupling partner, 43 mg (61%) of Example 38 was obtained after HPLC-purification. A gradient of 50 to 90% methanol over 20 min (against water and with 1% formic acid as additive) was used as mobile phase during the preparative HPLC-purification. [α]$_D$ −142 (c 0.25, HCO$_2$H); IR λ 1656, 1565, 1488, 1440, 1367, 698 cm$^{-1}$; $^1$H NMR (400 MHz, AcOH-d$_4$) δ 7.29-7.08 (m, 4H), 7.08-7.89 (m, 6H), 5.96 (d, J=8.0 Hz, 1H), 3.85 (dd, J=11.7, 8.0 Hz, 1H), 3.66 (d, J=11.7 Hz, 1H); $^{13}$C NMR (100 MHz, AcOH-d$_4$) δ 172.5, 154.9, 146.0, 137.8, 136.4, 133.5, 132.1, 130.7 (broad), 130.5 (broad), 130.1 (2C), 129.0 (2C, broad), 128.8, 128.6, 128.4 (2C), 124.6, 111.3, 63.8, 32.9; HRMS (FAB$^+$) calcd [M+H]$^+$ C$_{21}$H$_{16}$N$_3$O$_3$S$^+$ 390.0907, obsd 390.0912

Example 39

(7R)-6,7-dihydro-3-(4-methoxyphenyl)-4-phenyl-pyrazolo[4,5-d]thiazolo[3,2-a]pyridine-9-one-7-carboxylic acid By following the general procedure for Suzuki coupling of Example 36 using 55 mg (0.36 mmol) 4-methoxyphenylboronic acid as coupling partner, 40 mg (55%) of Example 39 was obtained after HPLC-purification. A gradient of 50 to 90% methanol over 20 min (against water and with 1% formic acid as additive) was used as mobile phase during the preparative HPLC-purification. [α]$_D$ −87 (c 0.25, HCO$_2$H); IR λ 1656, 1558, 1468, 1247, 1172, 1031, 829, 781, 698 cm$^{-1}$; $^1$H NMR (400 MHz, AcOH-d$_4$) δ 7.31-7.14 (m, 3H), 7.14-6.96 (m, 2H), 6.94 (d, J=8.7 Hz, 2H), 6.57 (d, J=8.7 Hz, 2H), 5.96 (d, J=8.1 Hz, 1H), 3.86 (dd, J=11.9, 8.1 Hz, 1H), 3.71 (s, 3H), 3.66 (d, J=11.9 Hz, 1H); $^{13}$C NMR (100 MHz, AcOH-d$_4$) δ 172.7, 160.4, 155.1, 145.8, 137.6, 136.5, 133.6, 131.4 (2C), 130.9 (broad), 130.5 (broad), 129.1 (2C, broad), 128.7, 124.5, 124.5, 114.0 (2C), 111.4, 63.8, 55.6, 32.9; HRMS (FAB$^+$) calcd [M+H]$^+$ C$_{22}$H$_{18}$N$_3$O$_4$S$^+$ 420.1013, obsd 420.1008

Example 40

(7R)-6,7-dihydro-3-(3-nitrophenyl)-4-phenyl-pyrazolo[4,5-d]thiazolo[3,2-a]pyridine-9-one-7-carboxylic acid By following the general procedure for Suzuki coupling of Example 36 using 60 mg (0.36 mmol) 3-nitrophenylboronic acid as coupling partner, 29 mg (37%) of Example 40 was obtained after HPLC-purification. A gradient of 50 to 90% methanol over 30 min (against water and with 1% formic acid as additive) was used as mobile phase during the preparative HPLC-purification. [α]$_D$ −157 (c 0.25, HCO$_2$H); IR λ 1658, 1529, 1348, 698, 686 cm$^-$; $^1$H NMR (400 MHz, MeOH-d$_4$) δ 7.99-7.94 (m, 1H), 7.70-7.66 (m, 1H), 7.48-7.43 (m, 1H), 7.32-7.25 (m, 1H), 7.21-7.05 (m, 3H), 7.02-6.86 (m, 2H), 5.79 (d, J=8.0 Hz, 1H), 3.85 (dd, J=11.5, 8.0 Hz, 1H), 3.61 (d, J=11.5 Hz, 1H); $^{13}$C NMR (100 MHz, MeOH-d$_4$) δ 171.3 (broad), 154.7 (broad), 148.7, 143.6 (broad), 138.7, 136.9, 135.9, 134.9 (broad), 134.3 (broad), 130.8 (2C, broad), 129.8, 129.6 (broad), 129.2 (broad), 128.7, 125.1, 124.8, 123.1, 109.5, 64.0 (broad), 33.3; HRMS (FAB$^+$) calcd [M+H]$^+$ C$_{21}$H$_{15}$N$_4$O$_5$S$^+$ 435.0758, obsd 435.0757

Example 41

(7R)-3-(3-furyl)-6,7-dihydro-4-phenyl-pyrazolo[4,5-d]thiazolo[3,2-a]pyridine-9-one-7-carboxylic acid By following the general procedure for Suzuki coupling of Example 36 using 40 mg (0.36 mmol) 3-furylboronic acid as coupling partner, 36 mg (53%) of Example 41 was obtained after HPLC-purification. A gradient of 50 to 75% methanol over 20 min (against water and with 1% formic acid as additive) was used as mobile phase during the preparative HPLC-purification. [α]$_D$ −144 (c 0.25, HCO$_2$H); IR λ 1658, 1554, 1164, 796, 698 cm$^-$; $^1$H NMR (400 MHz, AcOH-d$_4$) δ 7.50-7.31 (m, 4H), 7.31-7.22 (m, 2H), 6.56 (s, 1H), 6.29-6.27 (m, 1H), 5.99 (d, J=8.1 Hz, 1H), 3.91 (dd, J=11.9, 8.1 Hz, 1H), 3.70 (d, J=11.9 Hz, 1H); $^{13}$C NMR (100 MHz, AcOH-d$_4$) δ 172.6, 154.8, 143.3, 124.6, 138.3, 138.0, 136.8, 133.4, 131.3 (broad), 131.0 (broad), 129.5 (3C, broad), 124.7, 117.8, 111.3, 111.1, 63.9, 33.0; HRMS (FAB$^+$) calcd [M+H]$^+$ C$_{19}$H$_{14}$N$_3$O$_4$S$^+$ 380.0700, obsd 380.0697

Example 42

(7R)-6,7-dihydro-4-phenyl-3-(2-tolyl)-pyrazolo[4,5-d]thiazolo[3,2-a]pyridine-9-one-7-carboxylic acid By following the general procedure for Suzuki coupling of Example 36 using 49 mg (0.36 mmol) 2-tolylboronic acid as coupling partner and prolonged heating at 140° C. (in total 60 min), 23 mg (32%) of Example 42 was obtained after HPLC-purification. A gradient of 50 to 90% methanol over 20 min (against water and with 1% formic acid as additive) was used as mobile phase during the preparative HPLC-purification. [α]$_D$ −40 (c 0.25, HCO$_2$H); IR λ 1654, 1560, 759, 725, 698 cm$^{-1}$; $^1$H NMR (400 MHz, AcOH-d$_4$) δ 7.13-6.86 (m, 9H), 5.96 (d, J=8.1 Hz, 1H), 3.86 (dd, J=12.0, 8.1 Hz, 1H), 3.66 (d, J=12.0 Hz, 1H), 1.93 (s, 3H); $^{13}$C NMR (100 MHz, AcOH-d$_4$) δ 172.6, 155.1, 145.2, 138.3, 137.5, 135.3, 133.2, 132.1, 131.6, 130.4 (3C, broad), 129.4, 128.5 (3C, broad), 126.0, 125.7, 111.6, 63.8, 32.9, 20.2; HRMS (FAB$^+$) calcd [M+H]$^+$ C$_{22}$H$_{18}$N$_3$O$_3$S$^+$ 404.1063, obsd 404.1075

Aβ Aggregation Assay for Testing of Inhibition Amyloid Fibril Formation

Lyophilized Aβ 1-40 was dissolved to 500 μM in 4 mM NaOH and divided in two parts. One part was diluted to 20 μM in PBS (50 mM phosphate buffer pH 7.4 containing 100 mM NaCl) and coated onto an ELISA 96-well plate (Costar) for 1 h at room temperature. The plate was washed in PBS to remove unbound Aβ 1-40. Substances (in DMSO) were diluted with PBS to different concentrations in the Aβ 1-40 coated ELISA plate. The second part of NaOH-solubilized Aβ 1-40 was thereafter added to each well to yield a final concentration of 100 μM Aβ 1-40 and 5% DMSO. The plate was incubated at 37° C. with agitation (600 rpm) for 24 hours to allow aggregation of Aβ 1-40.

The Aβ-substance mix was after aggregation diluted 10 times with 25 μM Thioflavin T (ThT) in PBS. The ThT-fluorescence was detected immediately by excitation at 450 nm and emission at 482 nm. The ThT-fluorescence of Aβ 1-40 aggregated with substances was compared to the ThT-fluorescence of Aβ 1-40 aggregated in the presence of 5% DMSO.

Results from Aβ aggregation assay performed with compounds Examples 21, 37, and 39 are presented in FIG. 1. The compounds can be seen to interfere with the formation of amyloid fibrils.

Plasma Clot Lysis Assay for Testing of PAI-1 Inhibitors
Materials
Two-Chain tPA
CaCl$_2$, p.a. Stock solution 0.1 M in water.
Citrate, 0.13 M
Recombinant human PAI-1
PAI-1 inhibitors dissolved in 100% DMSO.
Experimental Procedures
Clot Lysis in Platelet-Poor Plasma Blood from healthy fat-fasting volunteers was collected into 0.13 M trisodium citrate, 9 parts blood to 1 part anticoagulant. The tubes were centrifuged at 2000×g, 20 min, at RT. The supernatant, ie, the platelet poor plasma was pooled, aliquoted and frozen at −85° C. until used. At the day of experiment the plasma was thawed in a water bath and temperated to 37° C. All other constituents, except t-PA, were prewarmed to 37° C. To each well on a microtiter plate, 25 μL CaCl$_2$, 25 μL PAI-1 or 25 μL PAI-1 vehicle, 20 μL saline and 5 μL drug or 5 μL vehicle (100% DMSO) were added. Plasma was mixed with cold t-PA solution in the relation 4 parts plasma with 1 part t-PA, just before adding 125 μL of this mixture to each well. The final concentration was 12.5 mM for $CaCl_2$, 10-13 ng/mL for PAI-1, 34 ng/mL for t-PA, and the compounds were tested at a final concentration range 0.1 nM to 0.25 mM. The final plasma concentration was 50%, as a result of the different additives. The plate, covered with a plastic lid, was placed in a Microplate reader (Molecular Devices, US) and gently shaken. The change in turbidity was immediately monitored as a change in absorbance at 405 nm at 37° C. Data points were collected at intervals of 2 min, during a period of 10 h. After finished reading, the absorbance data were transformed into files containing the time and absorbance values for each well. The clot longevity, ie, the time the clot exists, was determined as the time between clot formation, ie, positive $V_{max}$, and clot lysis, ie, negative $V_{max}$. The effect of the drugs, ie, shortening of the longevity for the clot, was expressed as the concentration at which a halving of the clot lysis time was reached, the $IC_{50}$ ($pIC_{50}$=–log $IC_{50}$). Control clot lysis time, set to 100%, was determined in the presence of PAI-1, and the maximal effect, ie, the shortest lysis time that can be reached under defined conditions in this system, in the absence of PAI-1 was set to 0%.

Compounds having a $pIC_{50}$ higher than 4 were considered as being active. The following $pIC_{50}$ values are presented:

| Example | $pIC_{50}$ |
| --- | --- |
| 21 | 4.6 |
| 22 | 4.7 |
| 23 | 4.8 |
| 24 | 4.6 |
| 25 | 4.9 |
| 27 | 4.1 |
| 28 | 4.3 |
| 29 | 5.2 |

The invention claimed is:

1. A compound of the formula (I), or (II):

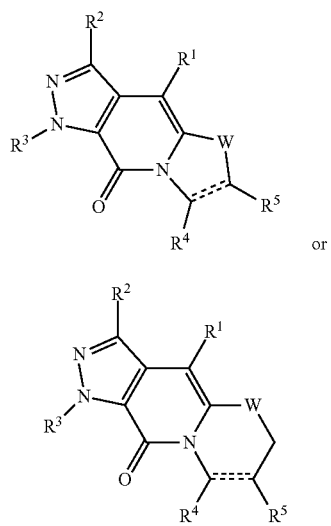

and pharmaceutically acceptable salts and enantiomers thereof,
wherein W is S;
$R^1$ is $(CH_2)_mD$ wherein m is a natural number being 0, 1, 2, 3, 4, or 5 and D is selected from the group consisting of unsubstituted and substituted aryl;

$R^2$ is $(CH_2)_nA$ wherein n is a natural number being 0, 1, 2, 3, 4, or 5 and A is selected from the group consisting of hydrogen, unsubstituted alkyl, unsubstituted substituted aryl, and furyl;

$R^3$ is $(CH_2)_nB$ wherein n is a natural number being 0, 1, 2, 3, 4, or 5 and B is selected from the group consisting of hydrogen and unsubstituted alkyl;

$R^4$ is $CO_2Y$, wherein Y is selected from the group consisting of hydrogen and unsubstituted alkyl $R^5$ is hydrogen.

2. The compound according to claim 1, of the formula (I) wherein
$R^1$ is $(CH_2)_mD$ wherein m is 0 and D is substituted aryl.

3. The compound according to claim 1, of the formula (I) wherein
$R^2$ is $(CH_2)_nA$ wherein n is 0, and A is hydrogen.

4. The compound according to claim 3, of the formula (I) wherein
$R^3$ is unsubstituted alkyl.

5. The compound according to claim 1, wherein aryl is $C_{6-15}$ aryl.

6. The compound according to claim 1 wherein substituted aryl is aryl substituted by one or more fluoro.

7. The compound according to claim 1 wherein substituted aryl is aryl substituted by one or more trifluoromethyl.

8. The compound according to claim 1 wherein substituted aryl is aryl substituted by one or more nitro.

9. The compound according to claim 1 wherein substituted aryl is aryl substituted by one or more methoxy.

10. A compound according to claim 1, of the formula (I), or (II), wherein the stereochemical configuration around the carbon which is covalently bound to $R_4$ is (R).

11. A compound according to claim 1, of the formula (I), or (II), wherein the stereochemical configuration around the carbon which is covalently bound to $R_4$ is (S).

12. The compound according to claim 1 which is selected from:
(7R)-3-isobutyl-9-oxo-4-[3-(trifluoromethyl)phenyl]-1,6,7,9-tetrahydropyrazolo[4,3-d][1,3]thiazolo[3,2-a]pyridine-7-carboxylic acid;
(7R)-9-oxo-3-propyl-4-[3-(trifluoromethyl)phenyl]-1,6,7,9-tetrahydropyrazolo[4,3-d][1,3]thiazolo[3,2-a]pyridine-7-carboxylic acid;
(7R)-9-oxo-3-pentyl-4-[3-(trifluoromethyl)phenyl]-1,6,7,9-tetrahydropyrazolo[4,3-d][1,3]thiazolo[3,2-a]pyridine-7-carboxylic acid;
(7R)-9-oxo-4-[3-(trifluoromethyl)phenyl]-1,6,7,9-tetrahydropyrazolo[4,3-d][1,3]thiazolo[3,2-a]pyridine-7-carboxylic acid;
(7R)-3-hexyl-9-oxo-4-[3-(trifluoromethyl)phenyl]-1,6,7,9-tetrahydropyrazolo[4,3-d][1,3]thiazolo[3,2-a]pyridine-7-carboxylic acid;
(7R)-1-ethyl-3-isobutyl-9-oxo-4-[3-(trifluoromethyl)phenyl]-1,6,7,9-tetrahydropyrazolo[4,3-d][1,3]thiazolo[3,2-a]pyridine-7-carboxylic acid; and,
(7R)-4-(3,4-difluorophenyl)-3-hexyl-9-oxo-1,6,7,9-tetrahydropyrazolo[4,3-d][1,3]thiazolo[3,2-a]pyridine-7-carboxylic acid.

13. The compound according to claim 1 which is selected from:
(7R)-6,7-dihydro-3-isobutyl-4-phenyl-pyrazolo[4,5-c]thiazolo[3,2-a]pyridine-9-one-7-carboxylic acid;
(7R)-6,7-dihydro-3,4-diphenyl-pyrazolo[4,5-c]thiazolo[3,2-a]pyridine-9-one-7-carboxylic acid;
(7R)-6,7-dihydro-3-(4-methoxyphenyl)-4-phenyl-pyrazolo[4,5-c]thiazolo[3,2-a]pyridine-9-one-7-carboxylic acid;
(7R)-6,7-dihydro-3-(3-nitrophenyl)-4-phenyl-pyrazolo[4,5-c]thiazolo[3,2-a]pyridine-9-one-7-carboxylic acid;

(7R)-3-(3-furyl)-6,7-dihydro-4-phenyl-pyrazolo[4,5-c]
thiazolo[3,2-a]pyridine-9-one-7-carboxylic acid; and (7R)-6,7-dihydro-4-phenyl-3-(2-tolyl)-pyrazolo[4,5-c]
thiazolo[3,2-a]pyridine-9-one-7-carboxylic acid.

14. A compound according to claim 1 for use in medicine.

15. A pharmaceutical formulation comprising a compound according to claim 1 in admixture with pharmaceutically acceptable adjuvants, diluents and/or carriers.

16. A method of inhibiting PAI-1, comprising contacting PAI-1 with an effective concentration of a compound of claim 1.

* * * * *

UNITED STATES PATENT AND TRADEMARK OFFICE
CERTIFICATE OF CORRECTION

| | |
|---|---|
| PATENT NO. | : 8,598,195 B2 |
| APPLICATION NO. | : 12/990415 |
| DATED | : December 3, 2013 |
| INVENTOR(S) | : Almqvist et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 405 days.

Signed and Sealed this
Eleventh Day of August, 2015

Michelle K. Lee
*Director of the United States Patent and Trademark Office*